US008454573B2

(12) United States Patent
Wyatt et al.

(10) Patent No.: US 8,454,573 B2
(45) Date of Patent: Jun. 4, 2013

(54) MEDICAMENT ADMINISTRATION APPARATUS

(76) Inventors: Philip Wyatt, Glendale, CA (US); Gary Schaeffer, Glendale, CA (US); Claude Vidal, Santa Barbara, CA (US); Wendy Elizabeth Wyatt, Glendale, CA (US)

( * ) Notice: Subject to any disclaimer, the term of this patent is extended or adjusted under 35 U.S.C. 154(b) by 269 days.

(21) Appl. No.: 12/928,545

(22) Filed: Dec. 13, 2010

(65) Prior Publication Data

US 2011/0160701 A1 Jun. 30, 2011

Related U.S. Application Data

(63) Continuation-in-part of application No. 12/151,345, filed on May 6, 2008, now abandoned.

(51) Int. Cl.
*A61M 5/32* (2006.01)
*A61M 25/16* (2006.01)

(52) U.S. Cl.
USPC ............................ 604/414; 604/411; 604/416

(58) Field of Classification Search
USPC .................................... 604/403, 411–416, 87
See application file for complete search history.

(56) References Cited

U.S. PATENT DOCUMENTS

| | | | | |
|---|---|---|---|---|
| 3,292,624 A | 12/1966 | Gabriel et al. | |
| 3,608,550 A * | 9/1971 | Stawski | 604/414 |
| 4,128,098 A * | 12/1978 | Bloom et al. | 604/406 |
| 4,215,690 A | 8/1980 | Oreopoulos et al. | |
| 4,588,403 A | 5/1986 | Weiss et al. | |
| 5,641,010 A * | 6/1997 | Maier | 141/329 |
| 6,478,788 B1 * | 11/2002 | Aneas | 604/411 |
| 6,524,278 B1 | 2/2003 | Campbell et al. | |
| 6,558,365 B2 * | 5/2003 | Zinger et al. | 604/410 |
| 6,699,229 B2 * | 3/2004 | Zinger et al. | 604/410 |
| 6,706,031 B2 * | 3/2004 | Manera | 604/411 |
| 6,832,994 B2 | 12/2004 | Niedospial, Jr. et al. | |

* cited by examiner

*Primary Examiner* — Leslie Deak
(74) *Attorney, Agent, or Firm* — James E. Brunton

(57) ABSTRACT

An apparatus for removal of premixed drugs or reconstitution of lyophilized drugs and for the injection of the reconstituted drug into the patient. The apparatus includes a syringe assembly and an adapter assembly that can be removably connected to a medicament container containing a premixed drug or lyophilized medicament. The syringe assembly of the apparatus includes a liquid chamber between the forward end of the body portion and the piston and a syringe cannula assembly. The syringe cannula assembly, which can be removably interconnected with the body portion, comprises a cannula support and a hypodermic needle sealably connected to the cannula support. The adapter assembly comprises an adapter preferably molded from a moldable plastic that includes a top wall, an adapter cannula connected to and extending from the top wall and a variety of connectors connected to the top wall for removably interconnecting the adapter with the medicament container. The adapter assembly further includes syringe connector member connected to the top wall for removably interconnecting the syringe with the adapter in a manner to uniquely position the syringe cannula within the lumen of the adapter cannula wherein it is completely shielded from external contamination to prevent print damage and injury to the user.

23 Claims, 17 Drawing Sheets

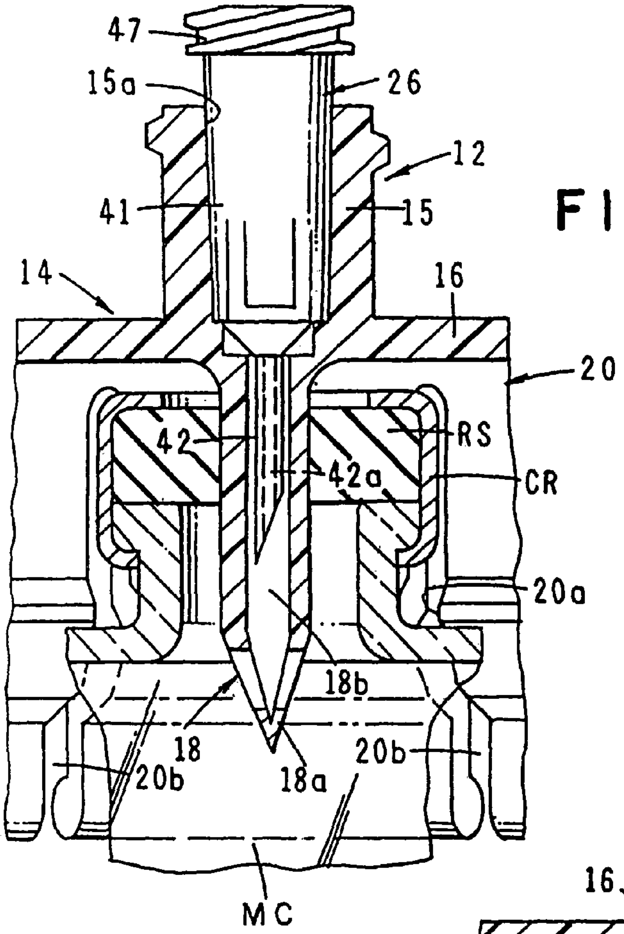
FIG. 2A
FIG. 4
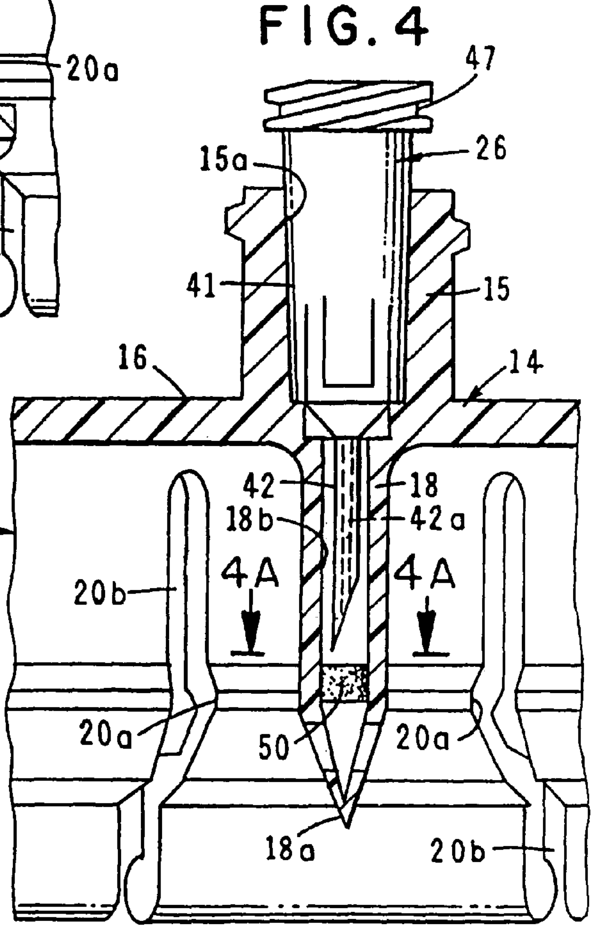
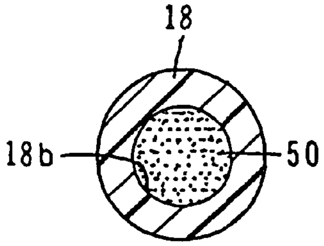
FIG. 4A

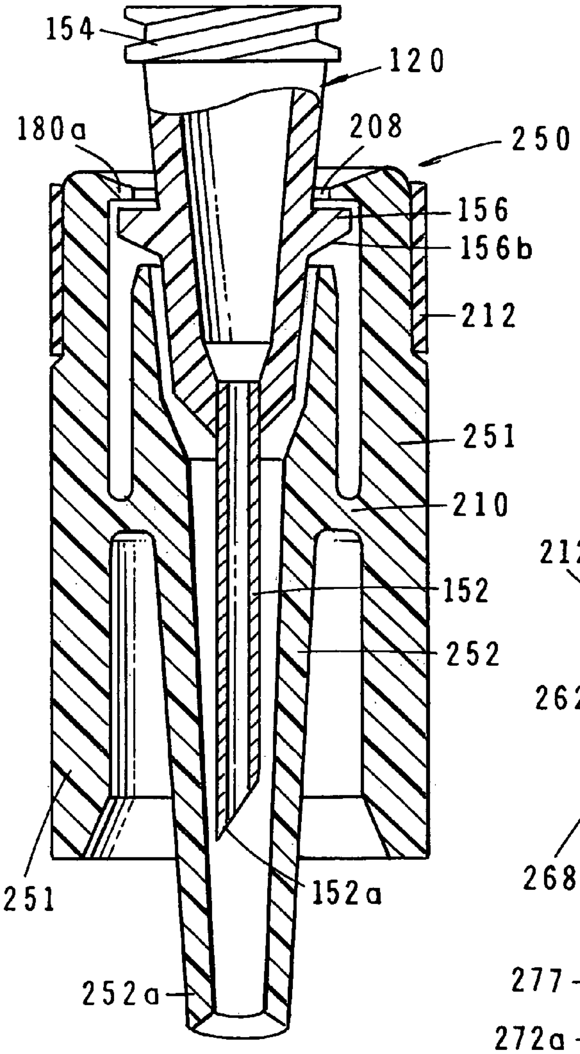
FIG. 23
FIG. 24
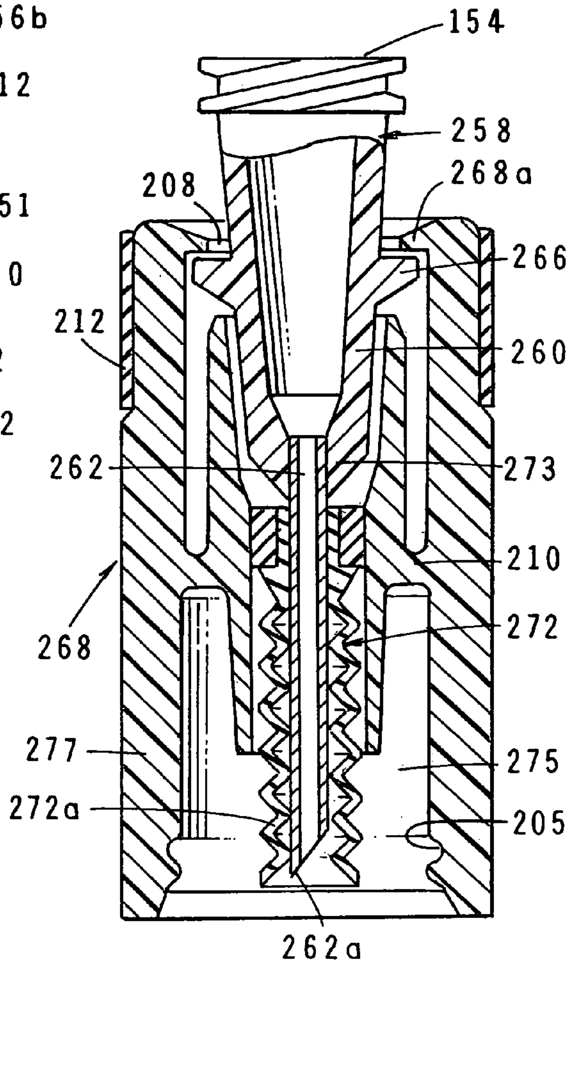

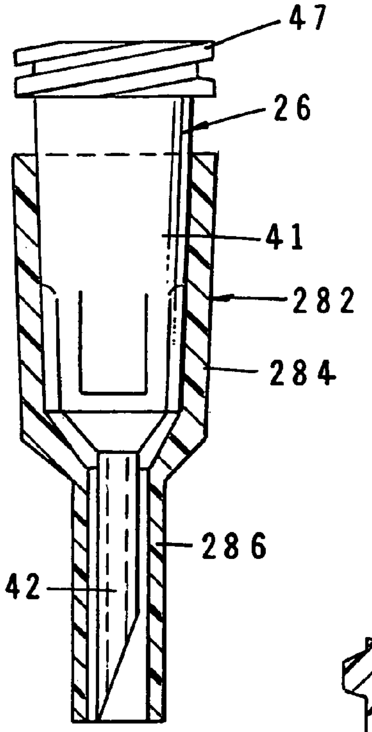
FIG. 26
FIG. 27
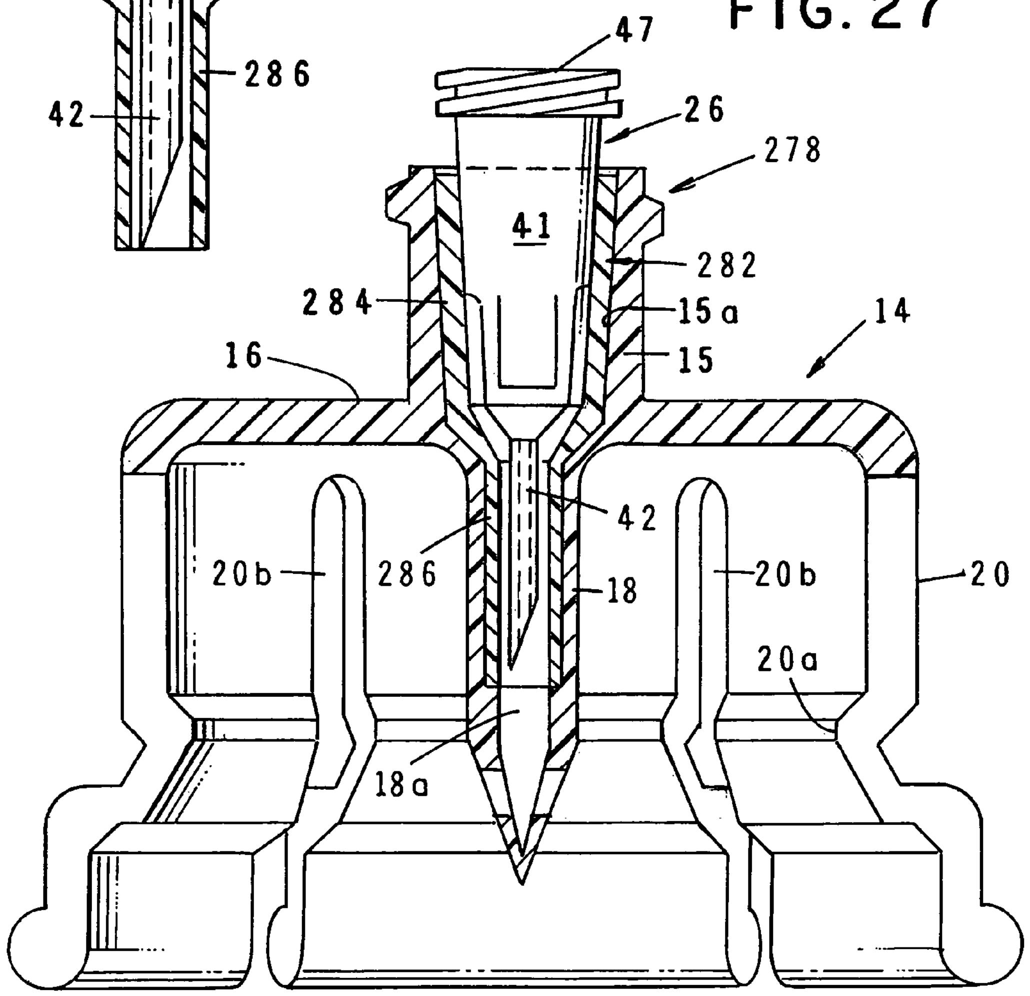

MEDICAMENT ADMINISTRATION APPARATUS

CROSS-REFERENCE TO RELATED APPLICATIONS

This is a Continuation-In-Part application of U.S. application Ser. No. 12/151,345 filed May 6, 2008 now abandoned.

STATEMENT REGARDING FEDERALLY SPONSORED RESEARCH OR DEVELOPMENT

Not Applicable

INCORPORATION-BY-REFERENCE OF MATERIAL SUBMITTED ON A COMPACT DISC

Not Applicable

BACKGROUND OF THE INVENTION

1. Field of the Invention

The present invention relates generally to medicament administration. More particularly, the invention concerns a novel fluid medicament delivery apparatus that is specially designed to facilitate the aseptic administration of drugs to patients.

2. Description of Related Art Including Information Disclosed Under 37 CFR 1.97 and 1.98

Medicaments intended for parenteral administration are typically stored in a medicament container in either in liquid, powdered or lyophilized form. Typically, lyophilized drugs are packaged in standard glass vials that are sealed with a pierceable rubber stopper and a crimped metal cap. A suitable liquid diluent must be added to the vial to reconstitute the powdered or lyophilized drug before use. In accordance with typical prior art methods, this reconstitution step was accomplished by drawing a measured amount of diluent, such as water, into a syringe from a diluent vial. The sealed vial containing the powdered or lyophilized drug was then accessed using a hypodermic needle and syringe to add the liquid diluent to the vial. The vial was then in inverted and shaken to intermix the drug with the liquid diluent. This done, the reconstituted drug was withdrawn into the syringe and was injected into the patient.

It is apparent that when reconstitution of a drug is required, the prior art processes required at least two fluid transfers. The problem of ensuring proper fluid transfer under acceptable aseptic conditions during these two fluid transfers was formidable and was especially acute in the case of self-administration of drugs by patients in a homecare environment. For example, during the fluid transfers, the rubber stopper that is disposed within the top of the vial must be penetrated by the syringe needle. Typically, the rubber stopper is not sterile and, accordingly, the exposed needle is exposed to non-sterile conditions. Furthermore, as the needle penetrates the rubber stopper it will inevitably become contaminated with small particles of rubber that are dislodged from the rubber stopper during the needle penetration step. Additionally, this two-step process is quite cumbersome for physicians and particularly for homecare caregivers to accomplish, often under the stressful conditions that frequently exist at the bedside of a patient.

One approach to overcoming the drawbacks of the prior art methods as described in the preceding paragraphs is disclosed in U.S. Pat. No. 6,238,372 to issued to Zinger et al. The Zinger et al. patent discloses a drug vial mixing and transfer device having one or more ports with interconnecting fluid passageways. The ends of the ports are attached either to a piercing connector or a syringe. The piercing connector is used to support and penetrate the rubber stoppers of the standard glass drug vials that are filled with powdered or lyophilized drugs or a liquid diluent during the transfer of the liquid diluent and drug solutions between the vials and the syringe. In one form of the invention, the ports and connectors are mounted on a base and a stopcock type valve is used to coordinate communication between the fluid passageways of the different ports. Retainers mounted on the base hold the syringe and vials in place during the liquid transfer operations.

BRIEF SUMMARY OF THE INVENTION

By way of summary, the present invention concerns a disposable shrouded vial adapter with a preconnected, integral “med push” hypodermic needle for low-cost, economical reconstitution of lyophilized drugs and for the direct injection of the reconstituted drug into the patient. In one form of the invention, the apparatus comprises a syringe assembly and a novel adapter assembly that can be removably connected to a medicament container or vial containing a liquid medicament, a powdered medicament or a lyophilized medicament. The syringe assembly of the apparatus includes an aspirator component that includes a body portion having a forward end and a piston slidably carried within the body portion to form a liquid chamber between the forward end of the body portion and the piston. The aspirator connector component of the syringe assembly, which comprises a syringe cannula assembly, is adapted to be removably interconnected with the aspirator component. This novel aspirator connector component comprises a cannula support and a syringe cannula connected to the cannula support.

In one form of the invention the adapter assembly comprises an adapter, preferably molded from a moldable plastic, that includes a body portion having a tapered bore, a top wall connected to the body portion, an adapter cannula connected to and extending from the body portion and a container connector means connected to the top wall for removably interconnecting the adapter with the medicament container. The container connector means can be of various configurations that telescopically receive and securely grip the upper portion of the medicament container. Uniquely, when the cannula support portion of the aspirator connector component is sealably received within the tapered bore of the body portion of the adapter assembly, the syringe cannula portion of the aspirator connector component is strategically positioned within the lumen of the adapter cannula where it is completely shielded from external contamination.

It is an object of the present invention to provide a method and apparatus for reconstituting a lyophilized drug and for then delivering the reconstituted drug to a patient. The method of the invention makes use of an apparatus of the character described in the preceding paragraph and is carried out in a manner such that the hypodermic syringe component of the apparatus is at all times protected from external contaminants and need not be used to penetrate the rubber stopper of the medicament container containing the drug that is to be reconstituted.

Another object of the invention is to provide a method of the aforementioned character in which off-the-shelf syringe body components that have been pre-filled with a suitable diluent can be used to accomplish the reconstitution step of the method of the invention.

Another object of the invention is to provide apparatus of the class described in which the adapter component includes filter means for filtering the fluid that is aspirated from the medicament container.

Another object of the invention is to provide apparatus of the class described in which the adapter component includes vent means for venting to atmosphere any gases that may be contained within the medicament container.

Another object of the invention is to provide an alternate form of the apparatus of the invention that comprises three cooperating components, namely a somewhat differently configured adapter component, a uniquely configured needle sheath for holding and protecting the needle and a differently configured a syringe connector assembly.

Another object of the invention is to provide apparatus of the character described in the preceding paragraph that includes a positive locking needle sheath that protects the user from accidental needle stick injury, from needle point damage and from needle point contamination when removed from the vial adapter in preparation for patent injection.

Another object of the invention is to provide apparatus of the character described in the preceding paragraphs that provides a cost-effective method for safely reconstituting a drug for use and for maintaining a safe environment during drug reconstitution and following removal of the needle from the vial adapter in preparation for patient injection.

Another object of the invention is to provide apparatus of the class described herein that is of a simple design and is easy use in both hospital and homecare environments.

Another object of the invention is to provide an apparatus as described in the preceding paragraph which can be inexpensively manufactured so that the apparatus can be economically disposed of after use.

Another object of the invention is to provide apparatus of the class described herein that can conveniently be used to reconstitute and deliver a wide variety of medicaments in various selected doses.

BRIEF DESCRIPTION OF SEVERAL VIEWS OF THE DRAWINGS

FIG. 2A is an enlarged view similar to FIG. 2, but illustrating in cross-section the area designated in FIG. 2 as 2A.

FIG. 4 is a fragmentary cross-sectional view of an alternate form of the vial accessing adapter subassembly of the apparatus of the invention that includes filter means for filtering the fluid withdrawn from the medicament container.

FIG. 4A is a greatly enlarged, cross-sectional view taken along lines 4A-4A of FIG. 4.

FIG. 23 is a cross-sectional view of an alternate form of needle sheath component of the vial accessing adapter subassembly of the invention.

FIG. 24 is a cross-sectional view of still another form of needle sheath component of the vial accessing adapter subassembly of the invention.

FIG. 26 is a cross-sectional view of yet another form of needle sheath component of the vial accessing adapter subassembly of the invention.

FIG. 27 is a side elevational view, partly in cross-section showing the form of vial accessing adapter subassembly of the invention that embodies the needle sheath component shown in FIG. 26.

DETAILED DESCRIPTION OF THE INVENTION

Figure 2:
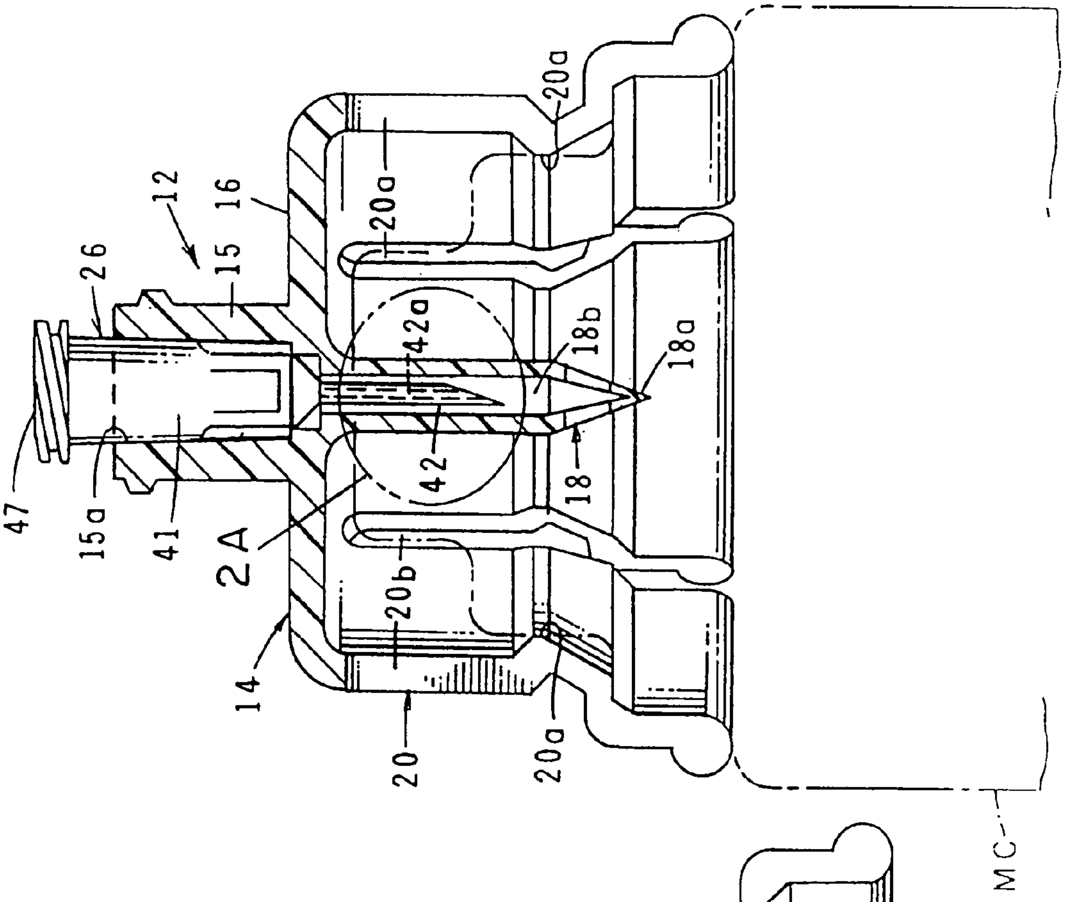
FIG. 2 is a view is similar to FIG. 1, but showing the vial accessing adapter subassembly positioned over and interconnected with a conventional medicament container or vial that is shown in phantom.
Figure 1:
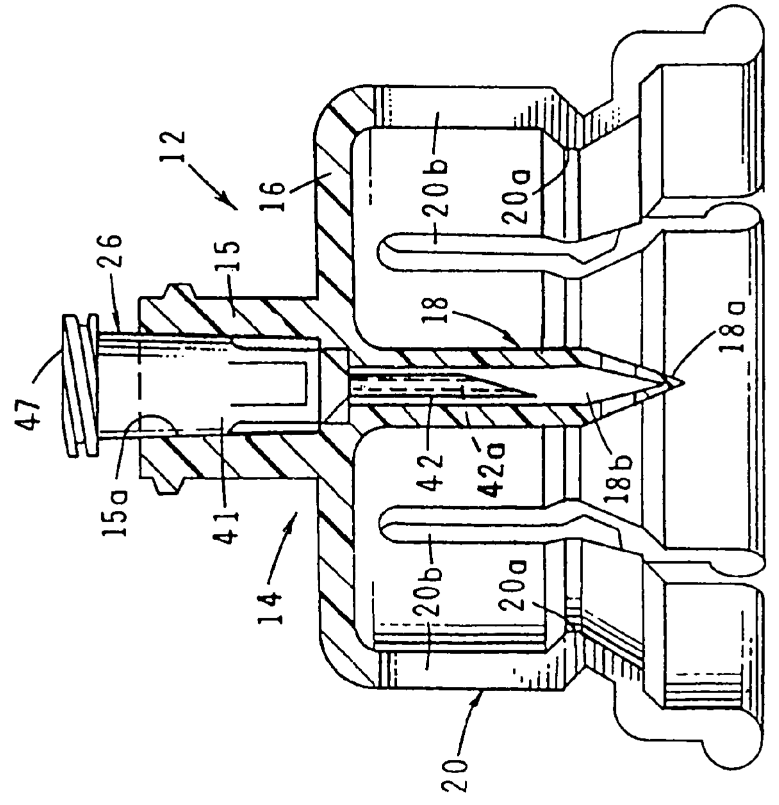
FIG. 1 is a side elevational view, partly in cross-section showing one form of the vial accessing adapter subassembly of the invention for use in administering medicaments to a patient.

Referring to the drawings and particularly to FIGS. 1 and 2, one form of the vial accessing adapter means of the invention for the aseptic administration of medicaments contained within a medicament container is there shown. The vial-accessing adapter means here comprises a vial accessing adapter subassembly 12 that includes an adapter component 14 that is preferably formed from a moldable plastic material. Adapter component 14 includes a body portion 15 having a tapered bore 15*a*, a top wall 16 connected to the body portion and an adapter cannula 18 that is integrally formed with and extends from body portion 15. A container connector means is also connected to top wall 16 and functions to removably interconnect the adapter component with a conventional medicament container MC (FIG. 2). The container connector means of the present form of the invention here comprises a resiliently deformable skirt 20 that is integrally formed with and extends from top wall 16 in the manner shown in the drawings. As best seen in FIG. 2, when the adapter component is mated with the medicament container, skirt 20 telescopically receives and securely grips the upper portion of the medicament container in a manner such that adapter cannula 18 will completely pierce the rubber stopper RS of the container (FIG. 2A). Rubber stopper RS is secured in position within the upper portion of the container in a conventional manner by a crimp ring CR.

As illustrated in FIG. 2A, plastic adapter cannula 18 has a piercing extremity 18*a* and a lumen 18*b* that communicates with the interior of the medicament container MC when the adapter component is interconnected with the container in the manner shown in FIG. 2A. In this regard, it is to be noted that skirt 20 is provided with a radially inwardly extending shoulder 20*a* and a plurality of circumferentially spaced slits 20*b* that enable the adapter component of the invention to be snapped over the upper portion of the medicament container MC to securely grip the container in the manner shown in FIG. 2.

Figure 3:
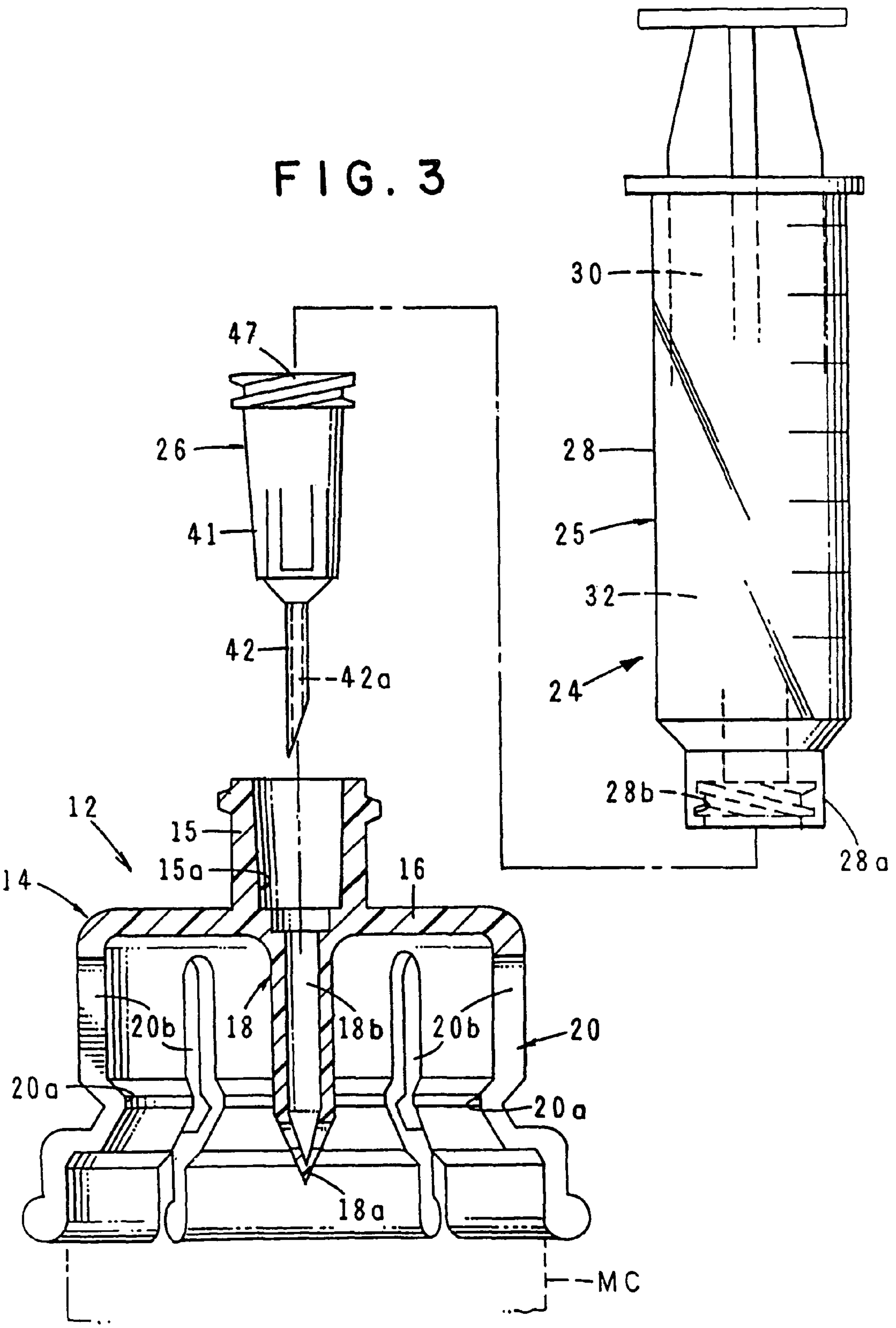
FIG. 3 is a view partly in cross section of the accessing adapter subassembly and the syringe body that can be operably interconnected with the accessing adapter subassembly to form the syringe assembly that is used to accomplish the fluid transfer steps.

In the present form of the invention, body portion 15 of the vial accessing adapter means functions to interconnect the syringe assembly 24 (FIG. 3A) of the apparatus of the invention with the medicament container MC. As illustrated in FIG. 3, this important syringe assembly 24 is made up of an aspirator means shown here as syringe body 25 and an aspirator connector means, or syringe cannula assembly 26, that can be sealably connected to body portion 15 of the vial accessing adapter means of the invention. The aspirator means or syringe body 25 includes a barrel portion 28 having a forward end 28*a* and a piston 30 that it is slidably carried within the barrel portion. As in conventional syringes, a liquid chamber 32 is formed between the forward end 28*a* of the barrel portion of the syringe body and piston 30.

Removably connected to the aspirator means or syringe body 25 is the previously mentioned aspirator connector means or syringe cannula assembly 26 that includes a syringe cannula support 41 and a syringe cannula 42 that is integrally formed with the syringe cannula support 41. As best seen in FIG. 2, syringe or aspirator cannula 42 is here shown as a hypodermic needle having a lumen 42*a*. As shown in FIG. 3, syringe cannula assembly 26, which is removably connected to syringe body portion 25 of the syringe assembly, is sealably receivable within the tapered bore 15*a* of body potion. It is important to note that when the syringe cannula support 41 of the cannula assembly 26 is sealably connected to body portion 15 in the manner shown in FIG. 2, the syringe cannula or hypodermic needle 42 is strategically positioned within lumen 18*a* of the adapter cannula 18 and is, therefore, protected from contamination, including contamination by the rubber stopper of the medicament container.

The syringe cannula support 41 of cannula assembly 26 is also provided with barrel connection means for connecting the assembly with the forward end 28 of the barrel portion 26 of the syringe body 25. This barrel connection means is here provided in the form of a conventional luer 48 formed on cannula support 41. As shown in the phantom lines of FIG. 3A, luer 48 is threadably receivable within internal threads 28*a* provided the forward end 28*b* of the barrel portion 28. Once the syringe cannula assembly 26 is interconnected with the syringe body 25, the syringe assembly 24 thus formed functions in the same manner as a conventional medicament administration syringe and, in the manner presently to be described, can be used to reconstitute lyophilized drugs and to administer medicaments to a patient in a conventional manner.

It is to be understood that the medicament container MC can contain a fluid medicament or, alternatively, can contain a medicament in a powdered or lyophilized form. As previously mentioned, when the medicament is in a powdered or lyophilized form a suitable liquid diluent must be added to the container to reconstitute the powdered or lyophilized drug before use. In accordance with one form of the method of the present invention, this can be accomplished by first accessing the sealed container of powdered or lyophilized drug using the vial accessing adapter means that is made up of adapter 14 and syringe cannula assembly 26. This accessing step is accomplished by placing the vial accessing adapter subassembly 12 over the medicament container MC and exerting a downward force on the subassembly sufficient to cause adapter cannula 18 to pierce the rubber stopper in the manner shown in FIG. 2A. With the components in the position shown in FIG. 2A, is to be observed that the lumen 18*a* of cannula 18 as well as the lumen 42*a* of piercing cannula 42 are in communication with the interior of medicament container MC.

With the vial accessing adapter subassembly 12 appropriately interconnected with the medicament container MC, the assemblage thus formed is inverted and a sealed syringe body 25 that has been prefilled with a suitable diluent opens and is then connected to the vial accessing adapter means by means of the luer connector 48 formed on member 41. The prefilled, sealed syringe body, which is a typically readily available, off-the-shelf item, can be of various sizes and can contain various types of diluent. With the prefilled syringe body connected to the vial accessing adapter subassembly, a force exerted on plunger 30 will cause the diluent to controllably flow into the medicament container MC. The inverted medicament container is then shaken to thoroughly intermix the powdered or lyophilized drug with the liquid diluent. This done, the reconstituted drug can be drawn into the syringe assembly 24 by withdrawing the plunger 30 of the syringe body. The syringe assembly 24 can then be removed from the adapter 14 and in the manner shown by the solid lines in FIG. 3A, the syringe can be used to administer the reconstituted drug to the patient. It is to be appreciated that throughout this entire process, cannula or hypodermic needle 42 has been maintained in a sterile configuration. Only cannula 18 has pierced the potentially contaminated rubber stopper RS of the medicament container and cannula 42 has been completely protected against any possible contamination by the rubber stopper RS. Stated another way, during the entire process of reconstituting the powdered or lyophilized drug, cannula 42 has been maintained in a virgin, sterile configuration and is completely free from any possible contamination at the time of administration of the reconstituted drug to the patient.

When the medicament to be delivered to the patient is contained within the medicament container and requires no reconstitution, the assembled syringe 24 can be mated with the adapter 14 and the assembly thus formed can be directly mated with the medicament container MC. In this instance, during the mating step, the skirt portion 20 of the adapter is snapped over the upper portion of the container and the cannula 18 is urged into piercing engagement with the rubber stopper in the manner shown in FIG. 2A so as to open communication between lumen 42*a* of cannula 42 and the interior of the medicament container MC. The syringe assembly can then be used to withdraw the liquid medicament from the container into reservoir 32 of the syringe assembly. The syringe assembly can then be removed from the adapter 14 and used to inject the medicament within reservoir 32 into a patient in a conventional manner. It is to be understood that, if desired, the syringe cannula assembly can first be connected to the adapter 14 to form a container accessing subassembly comprising the syringe cannula assembly and the adapter 14. The container accessing subassembly can then be mated with the medicament container so that the cannula 18 pierces the rubber stopper. This done, the syringe body can be mated with the container accessing subassembly and by sliding the piston outwardly of the syringe body, the medicament can be removed from the container.

Turning next to FIGS. 4 and 4A, there is shown an alternate form of the vial accessing adapter means of the apparatus of the invention for the aseptic administration of medicaments contained within a medicament container. This alternate form of the invention is quite similar to the embodiment shown in FIGS. 1 through 3 and like numerals are used in FIGS. 4 and 4A to identify like components. The primary difference between this latest form of the invention and the earlier described embodiment resides in the fact that a filter means, shown here as a porous filter 50, is provided within lumen 18*a* of cannula 18. Filter 50, which can be constructed from any suitable porous metal or ceramic material, is strategically positioned between cannula 42 and the open-end 18*a* of cannula 18. When positioned within cannula 18, filter 50 functions to effectively filter out any particular matter that may reside within the liquid medicament contained within medicament container MC.

Figure 5:
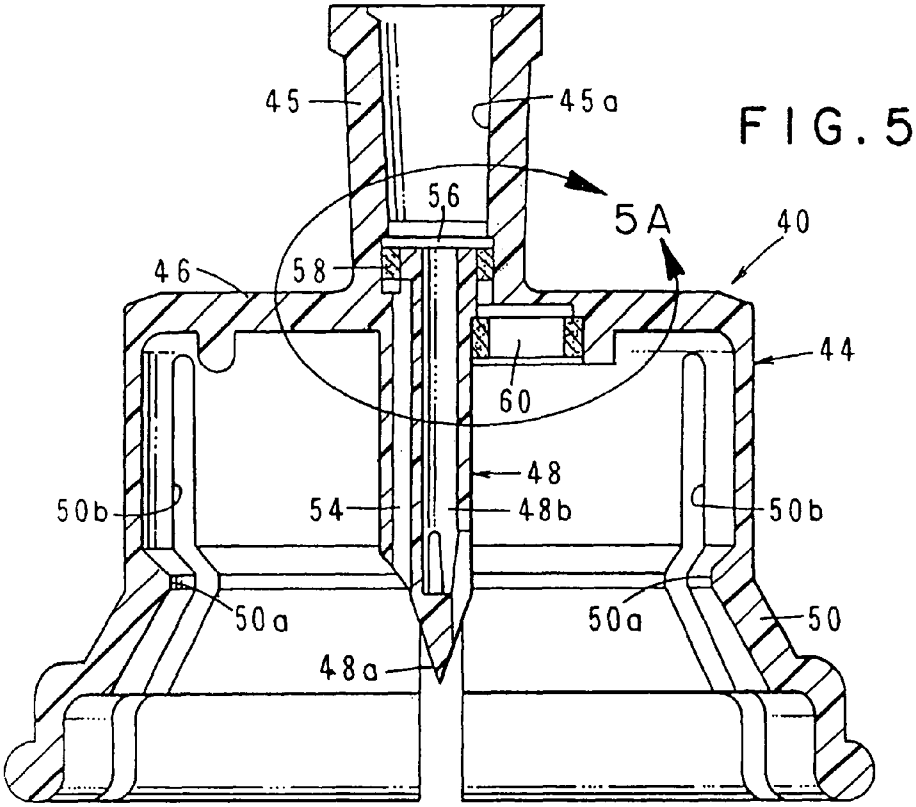
FIG. 5 is a cross-sectional view of another form of the adapter component of the vial accessing adapter means of the invention that includes venting means for venting to atmosphere gases contained within the medicament container.
Figure 5A:
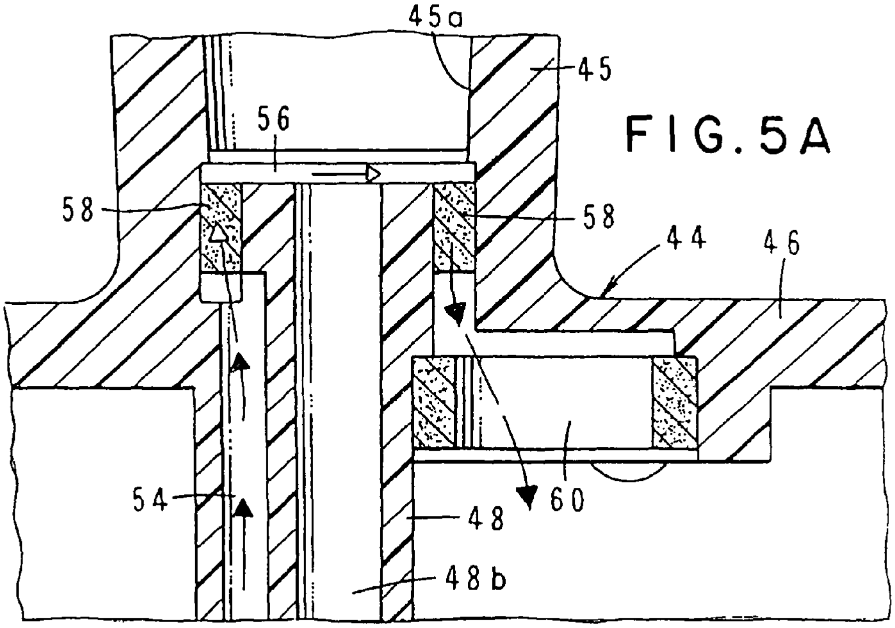
FIG. 5A is an enlarged, cross-sectional view of the area designated in FIG. 5 as 5A.

Referring next to FIGS. 5 and 5A, an alternate form of vial accessing adapter means of the invention is there shown and generally designated by the numeral 40. The vial accessing adapter means of this alternate form of the invention is somewhat similar to vial accessing adapter means of the embodiment of the invention shown in FIG. 1, but uniquely includes venting means for venting to atmosphere any gases that may reside within in the medicament container.

As shown in FIG. 5, this alternate form of vial accessing adapter means includes an adapter component 44 that is preferably formed from a moldable plastic material. Adapter 44 includes a body portion 45 having a tapered bore 45*a* and a top wall 46 connected to the body portion. An adapter cannula 48 is integrally formed with and extends from body portion 45. A container connector means is connected to top wall 46 for removably interconnecting the adapter component to a conventional medicament container MC, such as the container shown in FIG. 2. The container connector means of the present form of the invention here comprises a resiliently deformable skirt 50 that is integrally formed with and extends from top wall 46 in the manner shown in the drawings. When the adapter component is mated with the medicament container, skirt 50 telescopically receives and securely grips the upper portion of the medicament container in a manner such that adapter cannula 48 will completely pierce the rubber stopper of the container.

As before, plastic adapter cannula 48 has a piercing extremity 48*a* and a lumen 48*b* that communicates with the interior of the medicament container when the adapter is interconnected with the container in the manner previously discussed herein. In this regard, it is to be noted that as in the earlier described embodiments, skirt 50 is provided with a radially inwardly extending shoulder 50*a* and a plurality of circumferentially spaced slits 50*b* that enable the adapter of the invention to be snapped over the upper portion of the medicament container to securely grip the container in the manner shown in FIG. 2.

In this latest form of the invention, cannula 48 is provided with a vent passageway 54 that also communicates with the interior of the medicament container. As best seen in FIG. 5A, vent passageway 54 communicates with a transversally extending passageway 56 via a filter member 58. Transversally extending passageway 56, in turn, communicates with a vent port 60 formed in top wall 46 of the adapter 44. The vent passageways 54 and 56, along with vent port 60, comprise the venting means of the form of the invention shown in FIGS. 5 and 5A. With the construction shown in these figure drawings, after plastic cannula 48 has pierced the rubber stopper of the medicament container, gases within the container can flow to atmosphere in the direction of the arrows shown in FIG. 5A and thereby affectively vent the interior of the container to atmosphere.

Figure 3A:
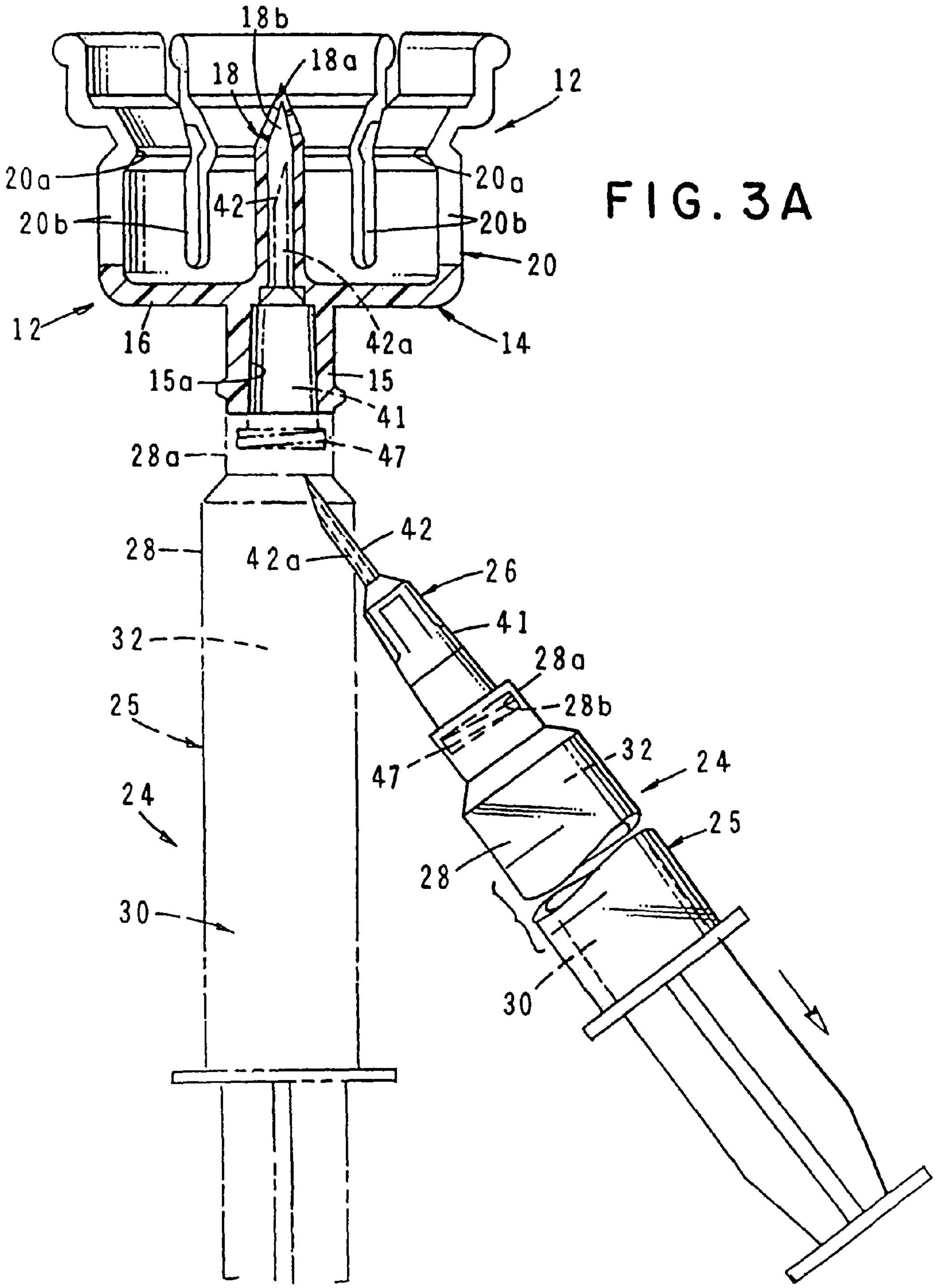
FIG. 3A is a view similar to FIG. 3, but showing the syringe assembly separated from the adapter component of the accessing adapter assembly.

As before, body portion 45 functions to removably interconnect a syringe assembly of the character previously described and as shown in FIG. 3A. As in the earlier described embodiments of the invention, the tapered bore 45*a* of body portion 45 is adapted to sealably receive the syringe cannula support 41 of the syringe cannula assembly 26, or aspirator connector means, that comprises cannula support 41 and syringe cannula 42 that is connected to the syringe cannula support 41. Once the aspirating means or syringe body 25 is interconnected with the syringe cannula support 41 in the manner previously described, the syringe assembly thus formed functions in the same manner as a conventional medicament administration syringe to reconstitute lyophilized drugs and to administer medicaments to a patient in a conventional manner.

Figure 6:
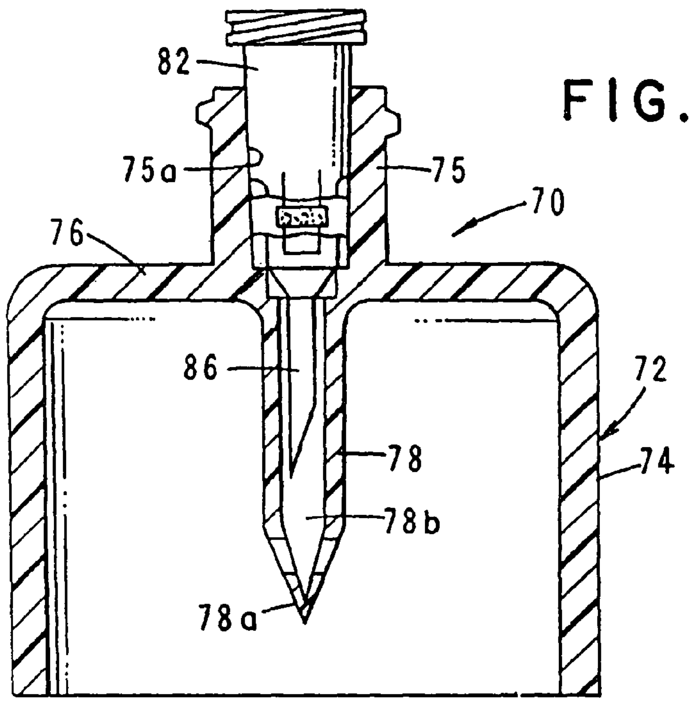
FIG. 6 is a cross-sectional view of still another form of the vial accessing adapter means of the invention having an adapter component of a different configuration.

Turning to FIG. 6, still another, alternate form of the vial accessing adapter means of the invention is there shown and generally designated by the numeral 70. The vial-accessing adapter means of this alternate form of the invention is also somewhat similar to that shown in FIG. 1, but uniquely comprises an adapter 72 that includes generally cylindrically shaped connector skirt 74. Adapter 72 also includes a body portion 75 having a tapered bore 75*a*, a top wall 76 connected to the body portion and an adapter cannula 78 that is integrally formed with and extends from body portion 75. Connector skirt 74 is connected to top wall 46 and functions to removably interconnect the adapter component to a conventional medicament container such as the container MC shown in FIG. 2. When the adapter component is mated with the medicament container, skirt 74 telescopically receives and securely grips the upper portion of the medicament container in a manner such that adapter cannula 78 will completely pierce the rubber stopper of the container.

As before, plastic adapter cannula 78 has a piercing extremity 78*a* and a lumen 78*b* that communicates with the interior of the medicament container when the adapter is interconnected with the container in the manner previously discussed herein.

The tapered bore 75*a* of body portion 75 is adapted to removably receive the syringe cannula support 82 of the syringe cannula assembly that comprises cannula support 82 and syringe cannula 86 that is connected to the syringe cannula support 82. Once the syringe body 25 is interconnected with the syringe cannula support 82 in the manner previously described, the syringe assembly thus formed functions in the same manner as a conventional medicament administration syringe to reconstitute lyophilized drugs and to administer medicaments to a patient in a conventional manner.

Figure 7:
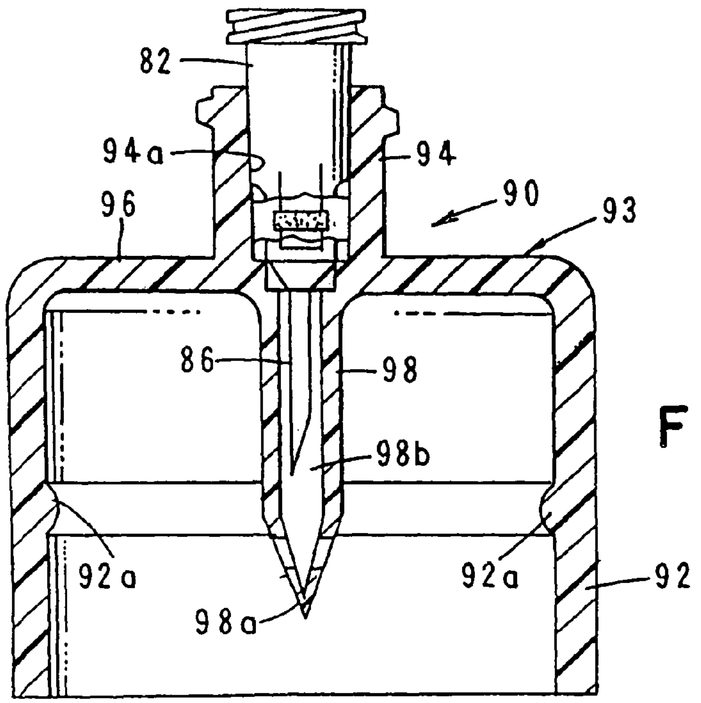
FIG. 7 is a cross-sectional view of yet another form of the vial accessing adapter means of the invention having an adapter component that includes a circumferentially extending, neck-gripping bead.

Referring next to FIG. 7, yet another alternate form of the vial accessing adapter means of the invention is there shown and generally designated by the numeral 90. The vial accessing adapter means of this alternate form of the invention is quite similar to that shown in FIG. 6 and like numerals are used in FIG. 7 to identify like components. The principal difference between the adapter means of the invention shown in FIG. 7 and that shown in FIG. 6 resides in the fact that the generally cylindrically shaped plastic skirt 92 of the adapter 93 is provided with a circumferentially extending protuberance 92*a*. When the adapter of this alternate form of the invention is interconnected with the medicament container, protuberance 92*a* is lockably received proximate the neck of the medicament container MC and functions to hold the adapter in position relative to the medicament container.

As in the earlier described embodiments, adapter 93 includes a top wall 96 and an adapter cannula 98 that is integrally formed with and extends from top wall 96. Connector skirt 92 is also connected to top wall 96 and functions to removably interconnect the adapter component to a conventional medicament container such as the container shown in FIG. 2. When the adapter component is mated with the medicament container, skirt 92 telescopically receives the upper portion of the medicament container and protuberance 92*a* grips the neck of the container in a manner such that adapter cannula 98 completely pierces the rubber stopper of the container.

As before, plastic adapter cannula 98 has a piercing extremity 98*a* and a lumen 98*b* that communicates with the interior of the medicament container when the adapter is interconnected with the container in the manner previously discussed herein.

Adapter 93 includes a body portion 94 to which the top wall 96 is connected, the body portion having a tapered bore 94*a*. Cannula 98 is integrally formed with and extends from body portion 94 so that when the adapter component is mated with the medicament container, the adapter cannula pierces the stopper of the medicament container. Skirt 92 telescopically receives and securely grips the upper portion of the medicament container and as in the earlier described embodiments of the invention, the body portion 94 functions to sealably receive a syringe cannula support 82 which is identical in construction and operation to that previously described.

Figure 8:
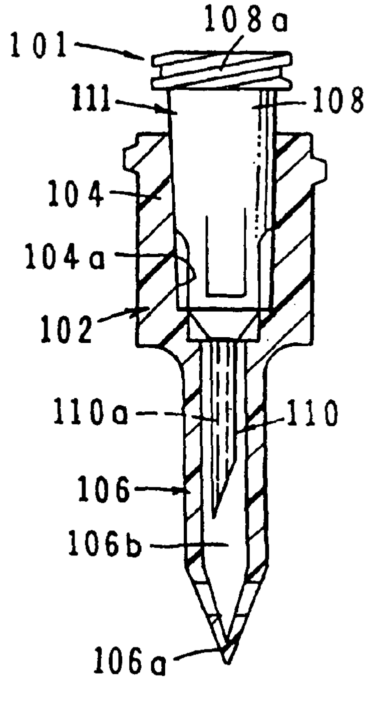
FIG. 8 is a cross-sectioned view of still another form of vial accessing adapter means of the invention for the aseptic administration of medicaments contained within a medicament container.

Turning to FIG. 8, still another form of vial accessing adapter means of the invention for the aseptic administration of medicaments contained within a medicament container is there shown and generally designated by the numeral 101. This latest form of the invention includes an adapter component 102 that is somewhat similar to the adapter 14 shown in FIG. 1, but does not include either a top wall or a resiliently deformable skirt for gripping the medicament container. Rather, the adapter component 102 includes only a generally cylindrically shaped body portion 104 that is similar in configuration to the previously described adapter body portions. This generally cylindrically shaped body portion 104 of adapter 101 is provided with a tapered bore 104*a* that is adapted to sealably receive a syringe cannula support 108 to which a syringe cannula 110 of a syringe cannula assembly 111 is connected. Connected to and depending from body portion 104, is an adapter cannula 106 having a piercing extremity 106*a* that is adapted to pierce the rubber stopper of a conventional medicament container. As shown in FIG. 8, adapter cannula 106 has a lumen 106*b* that is in communication with bore 104*a* of body portion 104.

Once again, it is important to note that when the syringe cannula support 108 of the aspirator connector means is sealably received within tapered bore 104*a* of body portion 104 in the manner shown in FIG. 8, the syringe cannula or hypodermic needle 110 is once again strategically positioned within lumen 106*b* of the adapter cannula 106 and is therefore protected from contamination. Once the syringe cannula assembly 111 is interconnected with an aspirating means, such as the earlier described syringe body 25 (FIG. 3), the syringe assembly thus formed functions in the same manner as a conventional medicament administration syringe and can be used to reconstitute lyophilized drugs and to administer medicaments to a patient in the manner previously described herein.

In accordance with an alternate form of the method of the invention for reconstituting a powdered or lyophilized drug, the sealed container containing the drug is first accessed using the vial accessing adapter subassembly 101, which is of the character shown in FIG. 8. This accessing step is accomplished by exerting a force on the subassembly 101 that is sufficient to cause adapter cannula 106 to pierce the rubber stopper so that the lumen 106*b* of cannula 106 as well as the lumen 110*a* of cannula 110 are in communication with the interior of the medicament container.

With the vial accessing adapter subassembly 101 appropriately interconnected with the medicament container, the assemblage thus formed is inverted and a sealed syringe body, such as syringe body 25 that has been prefilled with a suitable diluent is opened and is then connected to the vial accessing adapter subassembly 101 by means of the luer connector 108*a* formed on connector member 108. As before, the prefilled, sealed syringe body 25, or aspirator means, which is a typically readily available, off-the-shelf item, can be of various sizes and can contain various types of diluent. With the prefilled syringe body connected to the vial accessing adapter subassembly 101, a force exerted on the plunger of the syringe will cause the diluent to controllably flow into the medicament container. The inverted medicament container is then shaken to thoroughly intermix the powdered or lyophilized drug with the liquid diluent. This done, the reconstituted drug can be aspirated into the syringe assembly by withdrawing the plunger of the syringe body. The syringe assembly can then be removed from body 104 and the syringe can be used to administer the reconstituted drug to the patient.

It is to be appreciated that throughout this entire process, cannula or hypodermic needle 110 has been maintained in a sterile configuration. Only cannula 106 has pierced the rubber stopper of the medicament container and cannula 110 has been completely protected against any possible contamination by the rubber stopper of the medicament container.

When the medicament to be delivered to the patient is contained within the medicament container and requires no reconstitution, an assembled syringe, such as syringe 24, can be mated with body 104 of adapter 102 and the assembly thus formed can be directly mated with the medicament container. In this instance, during the mating step, the cannula 106 is urged into piercing engagement with the rubber stopper so as to open communication between lumen 106*b* of cannula 106 and the interior of the medicament container. The syringe assembly can then be used to withdraw the liquid medicament from the container into the reservoir of the syringe assembly. The syringe assembly can then be removed from body 104 and used to inject the medicament within the reservoir into a patient in a conventional manner.

Figure 9:
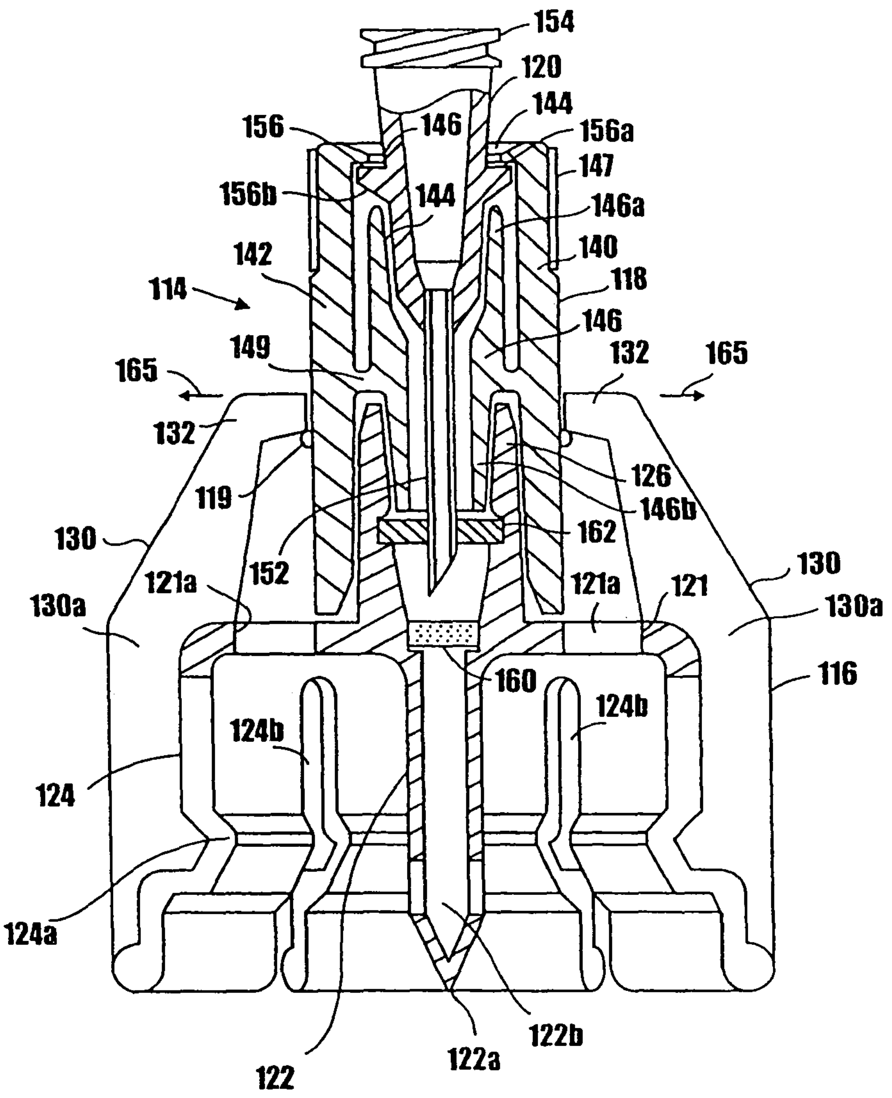
FIG. 9 is a cross-sectional view of yet another form of vial accessing adapter means for accessing a medicament container.

Turning now to FIG. 9, yet another alternate form of the vial accessing adapter means of the invention is there shown and generally designated by the numeral 114. The vial accessing adapter means of this latest form of the invention is somewhat similar to the earlier described embodiments of the invention. However, one form of this latest embodiment of the invention uniquely comprises three cooperating components, namely a somewhat differently configured adapter component 116, a uniquely configured needle sheath 118 and a differently configured a syringe, or aspirator connector assembly 120 that is adapted for interconnection with an aspirator. As will be discussed in greater detail hereinafter, in still another form of the invention, the needle sheath 118 and the aspirator connector assembly 120 are manufactured and provided to the user as a single, unitary assembly (see FIG. 12A).

Figure 13:
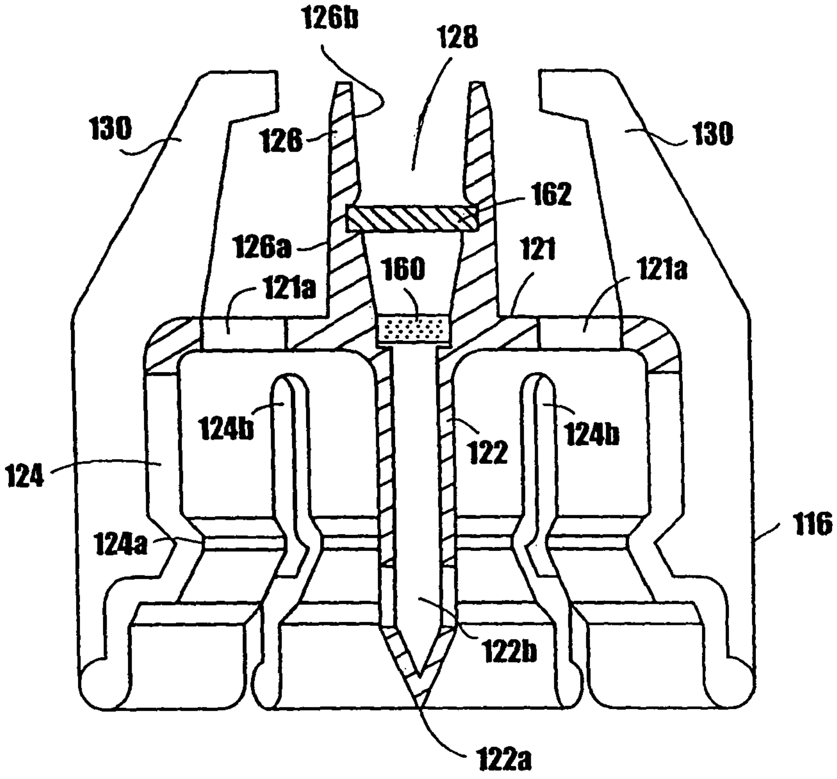
FIG. 13 is an enlarged cross-sectional view of the adapter component of the embodiment of the invention shown in FIG. 9.

As in the earlier described embodiments, adapter 116 includes a top wall 121 and an adapter cannula 122 that is integrally formed with and extends from top wall 121 (see also FIG. 13). Connected to and extending from top wall 121 in a first direction, is a resiliently deformable skirt 124 for receiving a portion of the medicament container. Skirt 124 functions to removably interconnect the adapter component to a conventional medicament container MC (FIG. 2). Skirt 124 is provided with a radially inwardly extending shoulder 124*a* and a plurality of circumferentially spaced slits 124*b* that enable the adapter component of the invention to be snapped over the upper portion of the medicament container MC. When the adapter component is mated with the medicament container, skirt 124 telescopically receives the upper portion of the medicament container and protuberance 124*a* grips the neck of the container in a manner such that adapter cannula 122 completely pierces the rubber stopper of the container. As before, plastic adapter cannula 122 has a piercing extremity 122*a* and a lumen 122*b* that communicates with the interior of the medicament container when the adapter is interconnected with the container in the manner previously discussed herein.

Connected to and extending from top wall 121 in a second direction, is a connector extension 126. As best seen in FIG. 13 of the drawings, connector extension 126 has an outer wall 126*a* and an inner wall 126*b* defining a bore 128.

Figure 14:
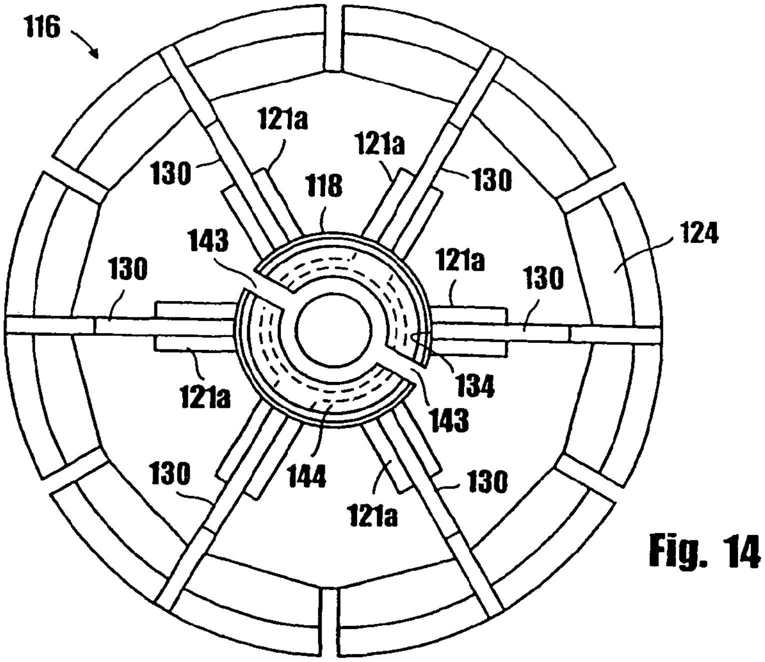
FIG. 14 is a top plan view of the assemblage made up of the adapter component and needle sheath subassembly of the embodiment of the invention shown in FIG. 9.
Figure 15:
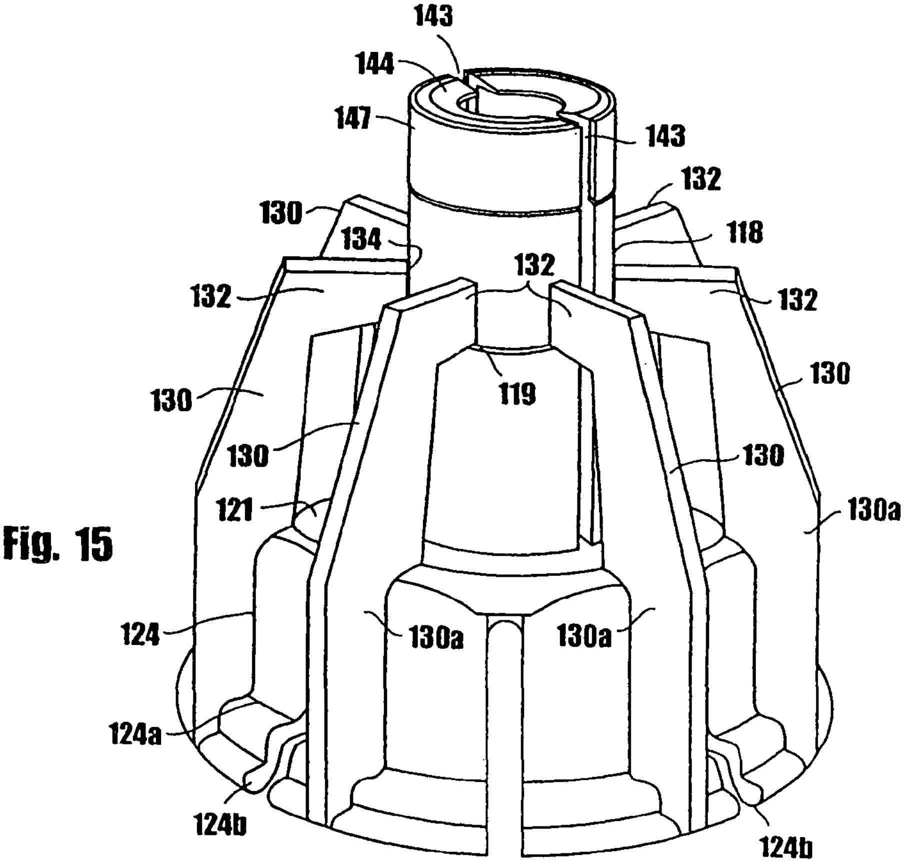
FIG. 15 is a generally perspective view of the assembly made up of the adapter component and needle sheath subassembly.

An important feature of this latest embodiment of the invention is the provision of a plurality of circumferentially spaced buttress members 130 that are connected to the resiliently deformable skirt 124 in the manner best seen in FIGS. 14 and 15. In the present form of the invention, six identically constructed buttress members are connected to the skirt 124 and each buttress member includes a body portion 130*a* that terminates in a radially inwardly extending finger 132 (FIG. 15). As best seen in FIG. 14 of the drawings, the plurality of buttress members cooperate to define a generally circular shaped opening 134. For a purpose presently to be described, each of the buttress members 130 is movable between a first closed position and a second open position. To enable the expeditious plastic molding of the adapter unit, top wall 121 is provided with clearance apertures 121*a*.

Forming still another important aspect of the vial accessing adapter means of this latest form of the invention is previously identified needle sheath assembly 118 that is closely received within the opening 134 defined by the six buttress members (FIGS. 9 and 15). In a manner presently to be described, this important needle sheath assembly 118 functions to lockably receive and protectively enclose the needle of the previously identified syringe connector assembly 120.

Figure 11:
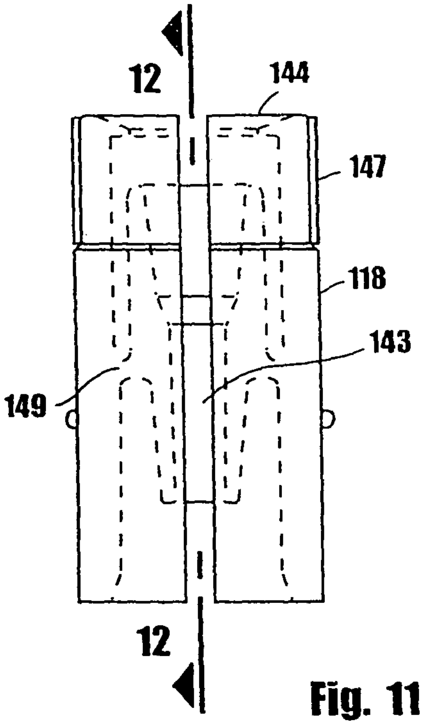
FIG. 11 is a side elevational view of the needle sheath subassembly of the embodiment of the invention shown in FIG. 9.
Figure 12:
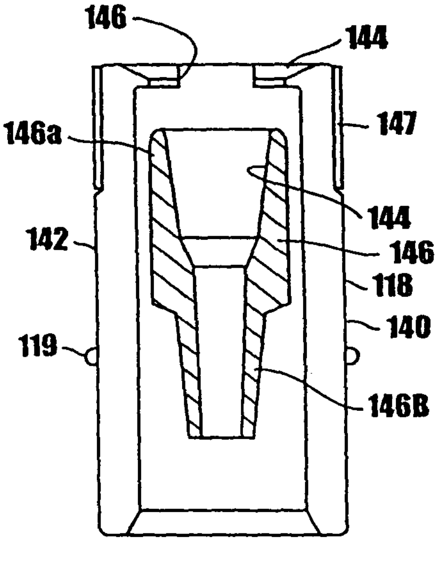
FIG. 12 is a cross-sectional view taken along lines 12-12 of FIG. 11.

Needle sheath assembly 118 which is preferably constructed from a moldable plastic, includes a needle sheath 140 having a yieldably deformable outer wall 142 that terminates in a generally annular shaped downwardly tapering locking flange 144 that defines an opening 146 (FIG. 12). In a manner presently to be described, yieldably deformable outer wall 142 that is provided with diametrically opposed longitudinally extending slits 143 (FIGS. 14 and 15) is movable against the urging of biasing means, here provided in the form of an elastomeric band 147 between a first closed position and a second open position to permit the insertion of the syringe connector assembly 120 into a passageway 144 defined by the upper portion 146*a* of an inner wall 146 of the needle sheath (FIG. 12). Inner wall 146 also includes a lower portion 146*b* which, as shown in FIG. 9, is closely received within the bore 128 defined by connector extension 126. As best seen in FIGS. 9 and 11 of the drawings, outer wall 140 of the needle sheath is interconnected with inner wall 146 by means of a fulcrum rib 149.

Figure 10:
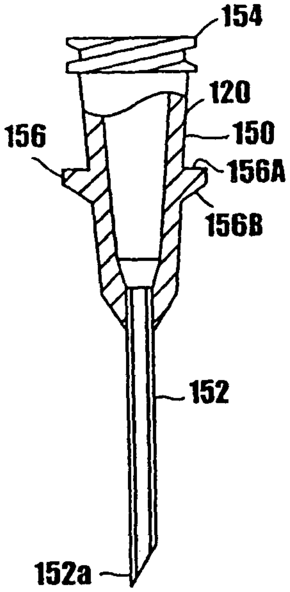
FIG. 10 is a cross-sectional view of one form of the aspirator connector means, or syringe cannula assembly of the embodiment of the invention shown in FIG. 9.

Referring particularly to FIGS. 9 and 10 of the drawings, aspirator or syringe connector assembly 120 can be seen to be somewhat similar in construction to the earlier described aspirator connector 26 of the invention (FIG. 3) and includes an outer wall 150 to which a downwardly extending hypodermic needle 152 having a piercing point 152*a* is connected. Provided proximate the upper end of outer wall 150 is a conventional luer connector 154 that permits the syringe connector assembly 120 to be interconnected with an appropriate aspirator such as the earlier described syringe 28 (FIG. 3). A unique feature of the syringe connector assembly, or aspirator connector 122, is the provision of a circumferentially extending, tapered locking rim 156 that functions to lockably engage the tapered flange 144 of the needle sheath when the aspirator connector is in position within the sheath 118 in the manner illustrated in FIG. 9 of the drawings. As illustrated in FIG. 9 of the drawings, locking rim 156 has an upper surface 156*a* that lockably engages flange 144 and a lower tapered surface 156*b*.

The vial accessing adapter means of this latest form of the invention also includes filter means, shown here as a particulate filter 160, for filtering particulate matter from medicament aspirated from the medicament container. Additionally, the vial accessing adapter means further includes a needle wiping member 162 that is connected to connector extension 126 in the manner best seen in FIG. 9 of the drawings.

In using the vial accessing adapter of the invention, the adapter 116 is first mated with the previously identified medicament container MC in the manner previously described. During the mating step, the skirt portion 124 of the adapter is snapped over the upper portion of the container and the adapter cannula 122 is urged into piercing engagement with the rubber stopper of the medicament container MC so as to open communication between the lumen of the cannula and the interior of the medicament container. This done, the needle sheath 118 is then mated with the adapter 116 by inserting the needle sheath into the opening 134 defined by the six circumferentially spaced apart buttress members 130. As the needle sheath is inserted into the opening 134, fingers 132 will be urged radially outwardly in the direction of the arrows 165 of FIG. 9, causing the protuberance 124*a* of the skirt 124 to be urged radially inwardly so as to securely grip the neck of the medicament container MC in a manner such that adapter cannula 122 completely pierces the rubber stopper of the container. As best seen in FIGS. 9 and 15, a circumferentially extending bead 119 is provided on the needle sheath 118 so that as the needle sheath is inserted into opening 134 and is moved downwardly into the position shown in FIG. 9, bead 119 will pass the buttress marking and impart a tactile sensation to the user indicating that the sheath is seated. As previously mentioned, as the needle sheath mates with the adapter, both the inner and outer walls of the needle sheath will sealably engage the inner surface of the connector extension 126.

Following mating of the needle sheath 118 with the adapter 116, the next step in this latest form of the method of the invention is to mate the syringe connector assembly 120 with the needle sheath 118. This is accomplished by inserting the lower body portion of the connector assembly into the opening 146 defined by the tapered flange 144 of the needle sheath and exerting a downward force on the connector assembly. This downward force will cause the tapered lower surface 156*b* of the connector assembly rim 156 to engage the tapered flange of the needle sheath in a manner to urge the outward movement of the deformable outer wall 142 relative to fulcrum 149 against the urging of the elastomeric band 147. As the deformable outer wall 142 moves into its open position, rim 156 will bypass the flange 144 and will move into the fully inserted position shown in FIG. 9 of the drawing and the elastomeric band 147 will urge the deformable outer wall 142 to return to its starting closed position. Movement of the connector assembly into a fully inserted position will cause the tapered outer wall of the connector assembly to move into sealing engagement with the inner surface of the upper portion of the inner wall 146 of the sheath 118. Movement of the connector assembly into a fully inserted position will also cause the needle 152 to pierce the elastomeric needle wiping member 162 in the manner shown in FIG. 9 of the drawings.

With the vial accessing adapter of the invention in the configuration shown in FIG. 9, medicament can be drawn from the medicament container MC in the manner previously described herein. As the medicament is drawn from the container, it will be suitably filtered by the particulate filter 160.

Figure 12A:
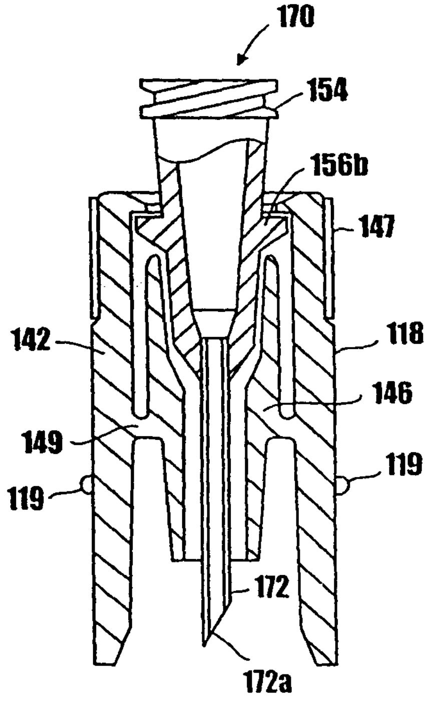
FIG. 12A is a cross-sectional view of the assemblage made up of the needle sheath assembly and the aspirator connector means.

As previously mentioned, in still another alternate form of the invention, the needle sheath 118 and the syringe connector assembly 120 are provided to the user as a single, unitary assembly (see FIG. 12A). In this instance, following mating the adapter 116 with the previously identified medicament container MC in the manner previously described, the assemblage made up of the needle sheath 118 and the syringe connector assembly 120 is then mated with the adapter 116 by inserting the assemblage into the opening 134 defined by the six circumferentially spaced apart buttress members 130. As the assemblage is inserted into the opening 134, fingers 132 will be urged radially outwardly in the direction of the arrows 165 of FIG. 9 causing the protuberance 124*a* of the skirt 124 to be urged radially inwardly so as to securely grip the neck of the medicament container MC. As illustrated in FIG. 9 of the drawings, as the assemblage is moved into the position shown in FIG. 9 of the drawings, bead 119 will pass the buttresses creating a tactile sensation and the needle 152 will pierce the elastomeric needle wiping member 162.

Following mating of the assemblage made up of the needle sheath 118 and the syringe connector assembly 120 with the adapter 116, the next step in this latest form of the method of the invention is to mate the syringe with the assemblage in the manner previously described so that the medicament can be drawn from the container and suitably filtered by the particulate filter 160.

It is apparent from a study of FIG. 9 that with the vial accessing adapter of the invention in the configuration shown in FIG. 9, the syringe connector assembly 120 is locked in position and cannot be removed from the needle sheath 118. Accordingly, when the user has finished filling the syringe, the assemblage made up of the syringe, the syringe connector assembly and the needle sheath can be separated from the adapter without using any special technique. This is made possible because the adapter will be securely held in place by the fact that the sheath outer walls 140 prevent the buttresses 132 from flexing inwardly. This, in turn, prevents surfaces 124*a* on the adapter legs from spreading out and freeing the adapter from the vial cap.

However, following removal from the adapter 116 of the assembly, made up of the needle sheath 118 and the syringe connector assembly 120, a radially inward force exerted on the lower portions of the deformable outer wall 142 will cause the upper portions of the outer wall of the needle sheath to move outwardly relative to fulcrum 149 against the urging of the elastomeric band 147. With the upper portions of the outer wall of the needle sheath in the open position, only then can the syringe connector assembly 120 be removed from the needle sheath. As the syringe connector assembly 120 is removed from the needle sheath, the needle 152 will be cleanly wiped by the needle wiping member 162, which here comprises a conventional elastomeric slit septum. Additionally, the septum advantageously seals the fluid access to the vial adapter once the needle sheath and the connector assembly are removed. This is doubly important with multiple-use applications where the user wants to maintain a sterile fluid path into the vial for repeated access, and also to essentially "seal" off the fluid path from the vial after use, preventing residual drug "mists" or leakage of dangerous or caustic drugs. Further, it is to be observed that the construction thus described provides a secure and tactile attachment in a closed system, once the device is attached to the drug vial. This closed system design significantly reduces the risk of any accidental drug "misting" or exposure to the outside air, especially important when working with dangerous or caustic drugs.

In yet another alternate form of the invention, the needle sheath 118, the syringe connector assembly 120 and the syringe are provided to the user as a single, unitary assembly. In this instance, following mating the adapter 116 with the previously identified medicament container MC in the manner previously described, the assemblage made up of the needle sheath 118, the syringe connector assembly 120 and the syringe is then mated with the adapter 116. This is accomplished by inserting the assemblage made up of the needle sheath 118 and the syringe connector assembly 120 into the opening 134 defined by the six circumferentially spaced apart buttress members 130. As this assemblage is inserted into the opening 134, fingers 132 will be urged radially outwardly in the direction of the arrows 165 of FIG. 9, causing the protuberance 124*a* of the skirt 124 to be urged radially inwardly so as to securely grip the neck of the medicament container MC. As illustrated in FIG. 9 of the drawings, as the assemblages moved into the position shown, the needle 152 will pierce the elastomeric needle wiping member 162.

Following mating of the assemblage made up of the needle sheath 118, the syringe connector assembly 120 and the syringe with the adapter 116, the next step in this latest form of the method of the invention is to withdraw the medicament from the container for later injection into the patient.

In accordance with one form of the method of the invention for reconstituting lyophilized medicaments and for the injecting the reconstituted medicaments into the patient using vial accessing means described in the preceding paragraphs, the first step in the method involves mating the adapter with the medicament container in a manner to place the adapter cannula in communication with the interior of the medicament container. This done, the aspirator is connected to the assembly made up of the needle sheath and the syringe connector assembly to form an aspiration assembly. Next, the assembly made up of the needle sheath and the syringe connector assembly is inserted into the opening defined by the buttress members. Using the aspirator containing a fluid, the fluid contained within the aspirator is caused to controllably flow into the medicament container and the medicament within the container is intermixed with the fluid to form a reconstituted medicament. Next, using the aspirator, the reconstituted medicament is withdrawn from the container and the aspiration assembly is removed from the adapter. The next step in the method of the invention uniquely involves yieldably deforming the wall of the needle sheath and removing the syringe connector assembly from the needle sheath to form a combination aspirator and syringe connector assembly. Finally, using the combination aspirator and syringe connector assembly, the reconstituted medicament is injected into the patient in a manner well understood by those skilled in the art.

In accordance with an alternate form of the method of the invention for injecting medicaments into the patient using vial accessing means described in the preceding paragraphs, the adapter is first mated with the medicament container in a manner to place the adapter cannula in communication with the interior of medicament container. This done, the aspirator is attached to the assembly made up of the needle sheath and the syringe connector assembly to form an aspiration assembly. Next, the assembly made up of the needle sheath and the syringe connector assembly is inserted into the opening defined by the buttress members and using the aspirator, the medicament is withdrawn from the container. Following withdrawal of the medicament from the container, the aspiration assembly is removed from the adapter. This done, the lower portion of the wall of the needle sheath is yieldably deformed so as to permit the removal of the syringe connector assembly from the needle sheath to form a combination aspirator and syringe connector assembly. Finally, using the combination aspirator and syringe connector assembly, the medicament is injected into the patient in a manner well understood by those skilled in the art.

Figure 10A:
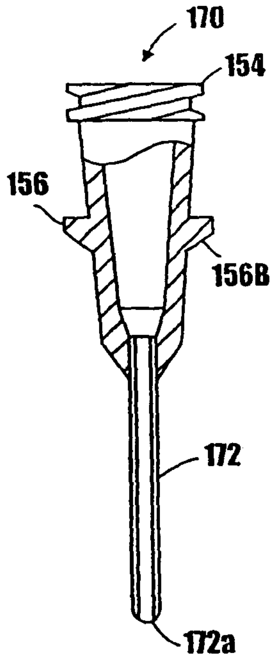
FIG. 10A is a cross-sectional view of an alternate form of the aspirator connector means, or syringe cannula assembly of the invention.

Turning to FIG. 10A of the drawings, an alternate form of the syringe connector assembly of the invention is there shown and generally designated by the numeral 170. Syringe connector assembly 170 is similar in construction and operation to previously identified syringe connector assembly 120 and like numerals are used in FIG. 10A to identify like elements. The primary difference between syringe connector assembly 120 and syringe connector assembly 170 resides in the fact that the piercing needle 172 is provided in the form of a blunt end cannula having a blunt piercing point 172*a*. Blunt end cannulas are well known in the art and are used with conventional slit septums of a character also well known in the prior art.

In using the vial accessing adapter means of the invention which embodies the piercing needle 172, following reconstitution of the drug in the manner previously described, instead of injecting the patient in a conventional manner with an injection needle having a sharp point, the caregiver will inject the drug into an intravenous "Y" site, or like injection site, that embodies a conventional slit septum or swabable valve.

Figure 17:
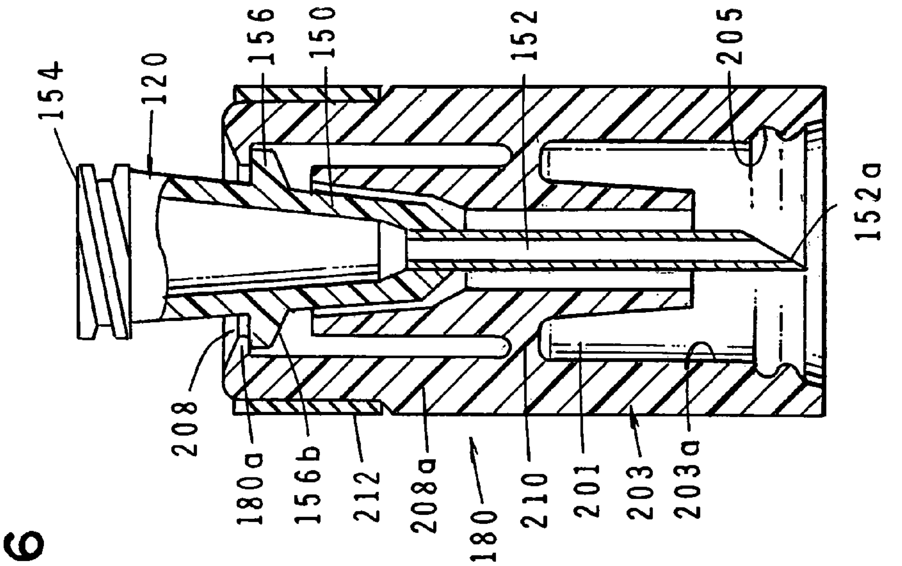
FIG. 17 is a side elevational exploded view, partly in cross-section of the vial accessing adapter subassembly illustrated in FIG. 16.
Figure 16:
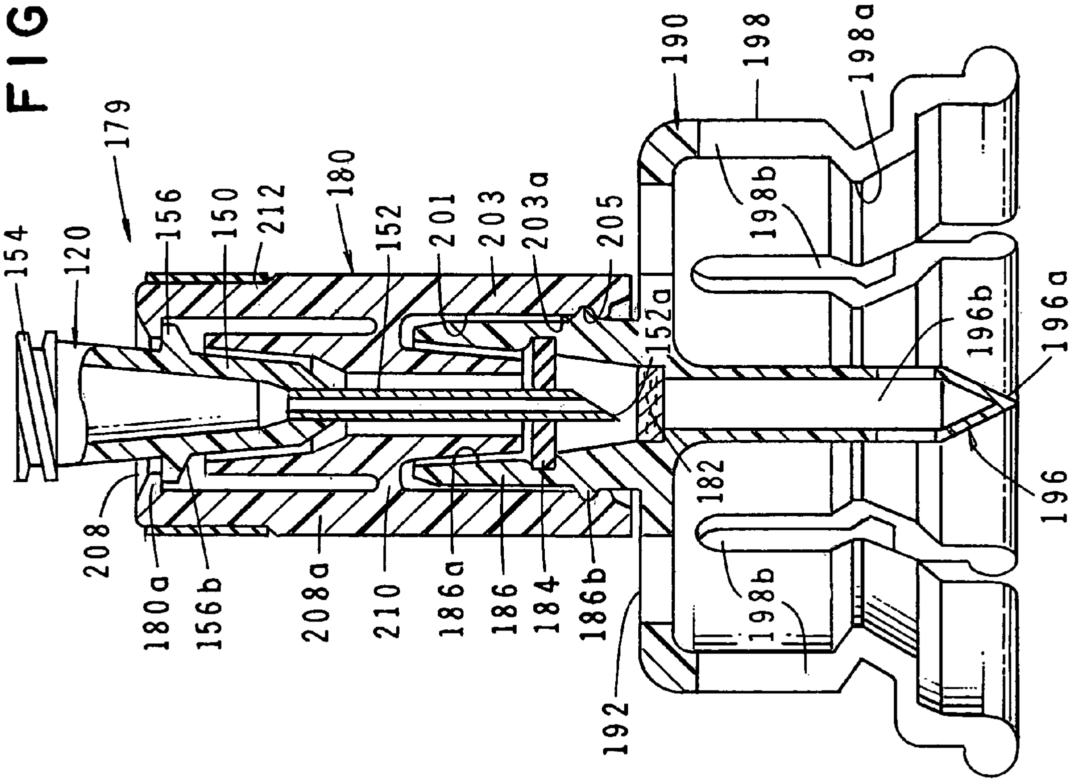
FIG. 16 is a side elevational view, partly in cross-section showing yet another form of the vial accessing adapter subassembly of the invention for use in administering medicaments to a patient.

Turning next to FIGS. 16 and 17, there is shown an alternate form of the vial accessing adapter means of the apparatus of the invention for the aseptic administration of medicaments contained within a medicament container. This alternate form of the invention, which is generally designated by the numeral 179, is somewhat similar to the embodiments shown in FIGS. 9 through 12A and like numerals are used in FIGS. 16 and 17 to identify like components. This latest form of the vial accessing adapter here comprises an aspirator, or syringe connector assembly 120 that includes an outer wall 150 to which a downwardly extending hypodermic needle 152 having a piercing point 152*a* is connected. Provided proximate the upper end of outer wall 150 is a conventional luer connector 154 that permits the syringe connector assembly 120 to be interconnected with an appropriate aspirator such as the earlier described syringe 28 (FIG. 3). As previously mentioned, a unique feature of the syringe connector assembly or aspirator connector 120, is the provision of a circumferentially extending, tapered locking rim 156 that functions to lockably engage the tapered flange 180*a* of the needle sheath 180 of the invention when the aspirator connector is in position within the sheath.

The vial accessing adapter means of this latest form of the invention also includes filter means, shown here as a particulate filter 182, for filtering particulate matter from medicament aspirated from the medicament container. Additionally, the vial accessing adapter means further includes a needle wiping member 184 that is connected to the neck portion 186 of the vial accessing adapter 190 of this latest form of the invention in the manner best seen in FIG. 16 of the drawings. An important feature of the apparatus of this latest form of the invention resides in the provision of a circumferentially extending protuberance 186*b* that is formed on the external surface of neck portion 186. The purpose of this protuberance will presently be described.

The vial accessing adapter 190 of this latest form of the invention which is preferably formed from a moldable plastic material, includes a top wall 192, the neck portion 186 that has a tapered bore 186*a* that is connected to the top wall and an adapter cannula 196 that is integrally formed with and extends from top wall 192. A container connector means is also connected to top wall 192 and functions to removably interconnect the adapter component with a conventional medicament container MC the character of which is shown in FIG. 2. The container connector means of this latest form of the invention here comprises a resiliently deformable skirt 198 that is integrally formed with and extends from top wall 192 in the manner shown in the drawings. When the adapter component is mated with the medicament container, skirt 198 telescopically receives and securely grips the upper portion of the medicament container in a manner such that adapter cannula 196 will completely pierce the rubber stopper RS of the container (FIG. 2A) so as to open communication between lumen of the cannula and the interior of the medicament container.

Once the vial accessing adapter 190 is mated with the medicament container, the needle sheath 180 is mated with the adapter 190 by inserting the neck portion 186 of the adapter into the opening 201 defined by the skirt portion 203 of the needle sheath 180. As best seen by referring to FIG. 17, the inner wall 203*a* of the skirt portion 203 of the needle sheath is provided with a circumferentially extending groove 205. As illustrated in FIG. 16 of the drawings, when the neck portion 186 of the adapter 190 is inserted into the opening 201, the previously mentioned circumferentially extending protuberance 186*b* that is formed on the neck portion 186 snaps into the groove 205 so as to securely lock together the needle sheath 180 and the vial accessing adapter 190.

Following mating of the needle sheath 180 with the vial accessing adapter 190, the syringe connector assembly 120 is mated with the needle sheath. This is accomplished by inserting the lower body portion of the connector assembly into the opening 208 defined by the tapered flange 180*a* of the needle sheath and exerting a downward force on the connector assembly. This downward force will cause the tapered lower surface 156*b* of the connector assembly rim 156 to engage the tapered flange of the needle sheath in a manner to urge the outward movement of the deformable outer wall 208*a* relative to fulcrum 210 against the urging of the elastomeric band 212. As the deformable outer wall 208 moves into its open position, rim 156 will bypass the flange 180*a* and will move into the fully inserted position shown in FIG. 16 of the drawing and the elastomeric band 212 will urge the deformable outer wall 208 to return to its starting closed position. Movement of the connector assembly into a fully inserted position will also cause the needle 152 to pierce the elastomeric needle wiping member 184 in the manner shown in FIG. 16 of the drawings.

With the vial accessing adapter of the invention in the configuration shown in FIG. 16, medicament can be drawn from the medicament container MC in the manner previously described herein. As the medicament is drawn from the container, it will be suitably filtered by the particulate filter 182.

As in the earlier described embodiments of the invention, plastic adapter cannula 196 has a piercing extremity 196*a* and a lumen 196*b* that communicates with the interior of the medicament container MC when the adapter component is interconnected with the container. In this regard, it is to be noted that skirt 198 is provided with a radially inwardly extending shoulder 198*a* and a plurality of circumferentially spaced slits 198*b* that enable the adapter component of the invention to be snapped over the upper portion of the medicament container MC to securely grip the container in the manner shown in FIG. 2.

Figure 19:
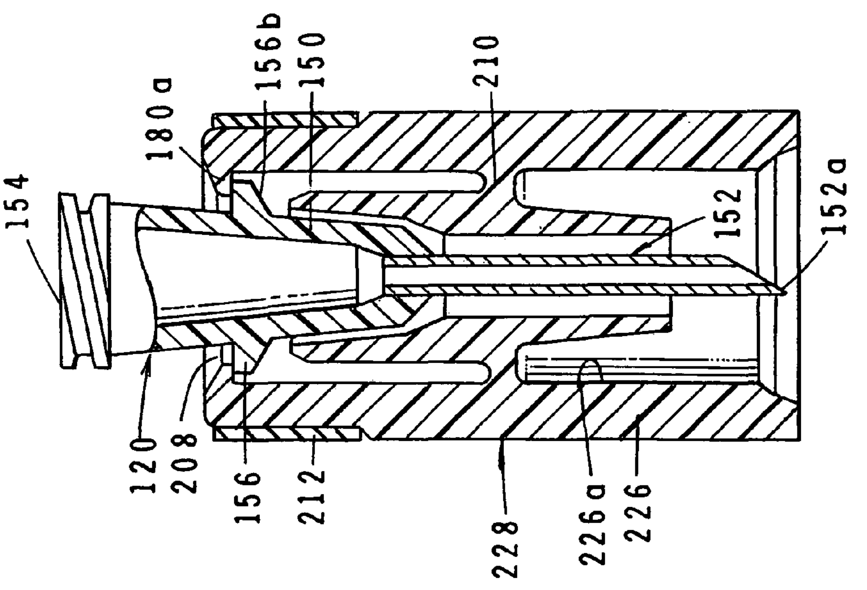
FIG. 19 is a side elevational exploded view, partly in cross-section of the vial accessing adapter subassembly illustrated in FIG. 18.
Figure 18:
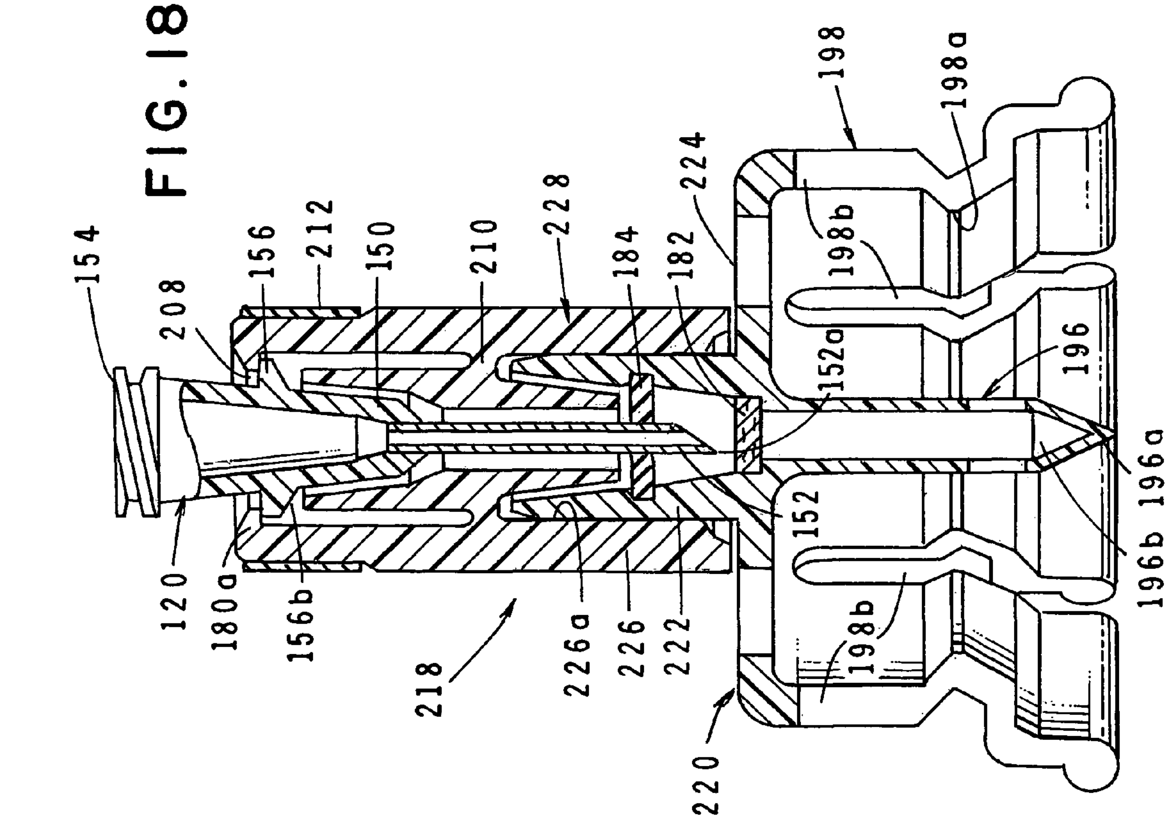
FIG. 18 is a side elevational view, partly in cross-section showing still another form of the vial accessing adapter subassembly of the invention for use in administering medicaments to a patient.

Referring next to FIGS. 18 and 19 of the drawings, yet another form of the vial accessing adapter means of the apparatus of the invention is there shown and generally designated by the numeral 218. This alternate form of the invention is quite similar to the embodiment shown in FIGS. 16 and 17 and like numerals are used in FIGS. 18 and 19 to identify like components. The primary difference between this latest form of the invention in the embodiment shown in FIGS. 16 and 17 resides in the fact that, as will presently be described, the vial accessing adapter is securely interconnected with the needle sheath by the frictional engagement between the outer wall of the neck portion of the vial accessing adapter and the inner wall of the skirt portion of the needle sheath.

As best seen in FIG. 19 of the drawings, the aspirator or syringe connector assembly 120 of this latest form of the invention is substantially identical in construction and operation to that of the embodiment of FIGS. 16 and 17. Similarly, the vial accessing adapter 220 of this latest form of the invention is substantially identical in construction and operation to the vial accessing adapter 190 save for the fact that the outer wall of the neck portion 222 is not provided with a circumferentially extending protuberance, such as protuberance 186*b* of the earlier described embodiment. Rather, the outer wall of the neck portion 222, which is connected to top wall 224, is tapered so that when the vial accessing adapter is mated with the needle sheath of this latest embodiment in the manner shown in FIG. 18, it will move into close frictional engagement with the inner wall 226*a* of the skirt portion 226 of the needle sheath 228. In view of this novel construction, in this latest embodiment of the invention the inner wall 226*a* of the skirt portion is not provided with a circumferentially extending groove and the vial accessing adapter is securely interconnected with the needle sheath by the frictional engagement between the outer wall of the neck portion 222 of the vial accessing adapter and the inner wall 226*a* of the skirt portion 226 of the needle sheath.

With the vial accessing adapter of the invention in the configuration shown in FIG. 18, medicament can be drawn from the medicament container MC in the manner previously described herein. As the medicament is drawn from the container, it will be suitably filtered by the particulate filter 182.

Figure 21:
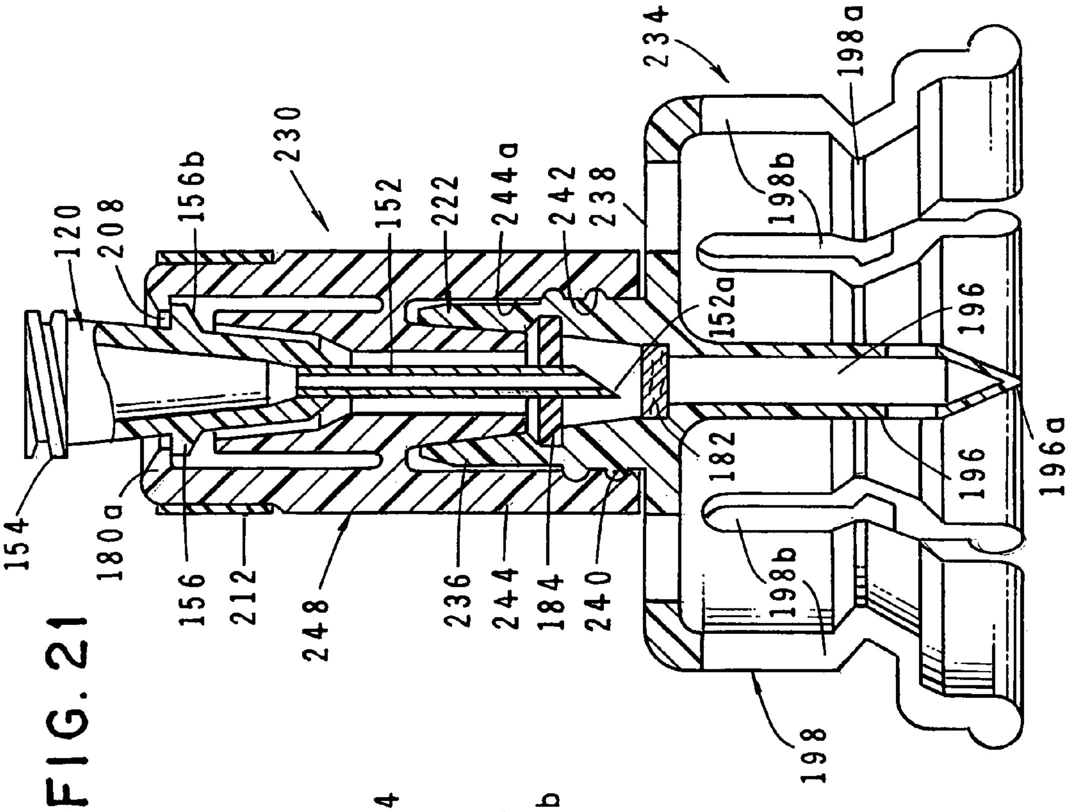
FIG. 21 is a side elevational view, partly in cross-section showing the form of vial accessing adapter subassembly of the invention that embodies the adapter component shown in FIG. 20.
Figure 20:
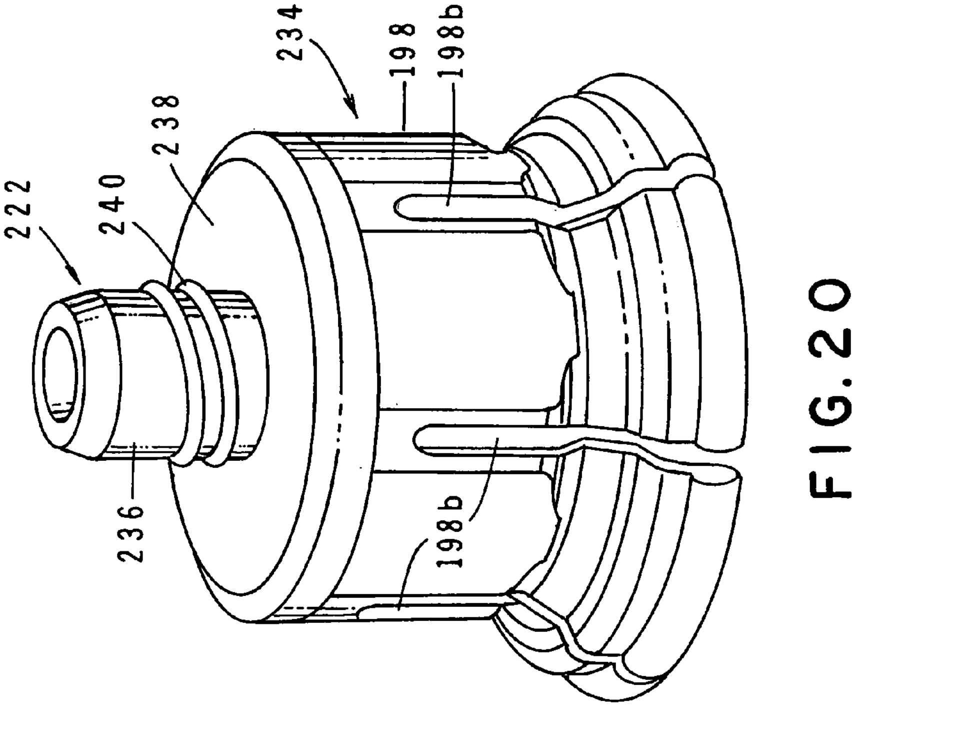
FIG. 20 is a generally perspective view of yet another form of the adapter component of yet another form of the vial accessing adapter subassembly of the invention.
Figure 22:
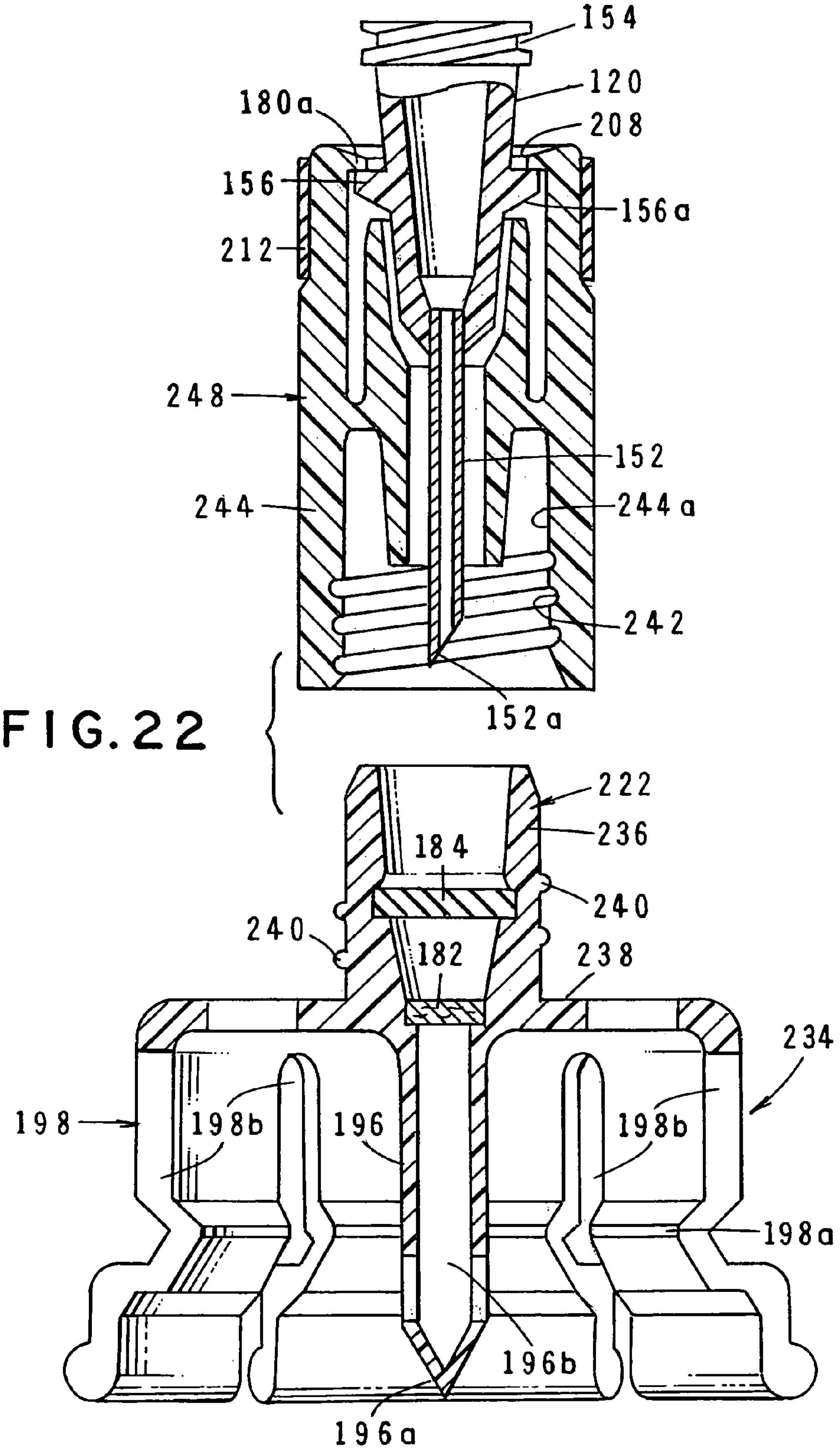
FIG. 22 is a side elevational exploded view, partly in cross-section of the vial accessing adapter subassembly illustrated in FIG. 21.

Turning now to FIGS. 20, 21 and 22 of the drawings, still another form of the vial accessing adapter means of the apparatus of the invention is there shown and generally designated by the numeral 230. This alternate form of the invention is also somewhat similar to the embodiment shown in FIGS. 16 and 17 and like numerals are used in FIGS. 20 through 22 to identify like components. The primary difference between this latest form of the invention and the embodiment shown in FIGS. 16 and 17 resides in the fact that, as will presently be described, the vial accessing adapter is securely interconnected with the needle sheath by means of a threaded connection.

As best seen in FIG. 22 of the drawings, the aspirator or syringe connector assembly 120 of this latest form of the invention is substantially identical in construction and operation to that of the embodiment of FIGS. 16 and 17. Similarly, the vial accessing adapter 234 of this latest form of the invention is substantially identical in construction and operation to the vial accessing adapter 190 save for the fact that the outer wall of the neck portion 236 is not provided with a circumferentially extending protuberance, such as protuberance 186*b* of the embodiment of FIG. 17. Rather, the outer wall of the neck portion, which is connected to top wall 238, is provided with an external thread 240, which in a manner presently to be described, threadably mates with an internal thread 242 that is formed on the inner wall 244*a* of the skirt portion 244 of the needle sheath 248 of this latest embodiment of the invention.

When the vial accessing adapter is mated with the needle sheath 248 of this latest embodiment in the manner shown in FIG. 21, external thread 240 of the vial accessing adapter will be received within internal thread 242 of the needle sheath in a manner to securely interconnect the components.

With the vial accessing adapter of the invention in the configuration shown in FIG. 21, medicament can be drawn from the medicament container MC in the manner previously described herein. As the medicament is drawn from the container, it will be suitably filtered by the particulate filter 182.

As in the earlier described embodiments of the invention, plastic adapter cannula 196 has a piercing extremity 196*a* and a lumen 196*b* that communicates with the interior of the medicament container MC when the adapter component is interconnected with the container. In this regard, it is to be noted that skirt 198 is provided with a radially inwardly extending shoulder 198*a* and a plurality of circumferentially spaced slits 198*b* that enable the adapter component of the invention to be snapped over the upper portion of the medicament container MC to securely grip the container in the manner shown in FIG. 2.

Referring next to FIG. 23 of the drawings, yet another form of the needle sheath of the apparatus of the invention is there shown and generally designated by the numeral 250. This alternate form of needle sheath is quite similar to the previously described needle sheaths of the invention and like numerals are used in FIG. 23 to identify like components. The primary difference between this latest form of the needle sheath and those previously described herein resides in the absence of protuberance 186*b* and in the differently configured inner wall, the lower portion of said inner wall thereof which here extends well beyond said lower portion of the outer wall 251 of the needle sheath and which encapsulates said needle 152 of the aspirator connector. More particularly, the lower portion 252*a* of the inner wall 252 is considerably elongated so as to extend well beyond the lower portion of the outer wall 251 of the needle sheath and well beyond the needlepoint 152*a* of the needle. With this novel construction, the elongated lower portion 252*a* of the inner wall 252 functions to protect the needlepoint 152*a* from contamination and also ensures that the needlepoint retains its sharpness. Additionally, the elongated lower portion 252*a* of the inner wall provides a useful means for interconnecting the needle sheath with ampules of conventional construction.

Figure 25:
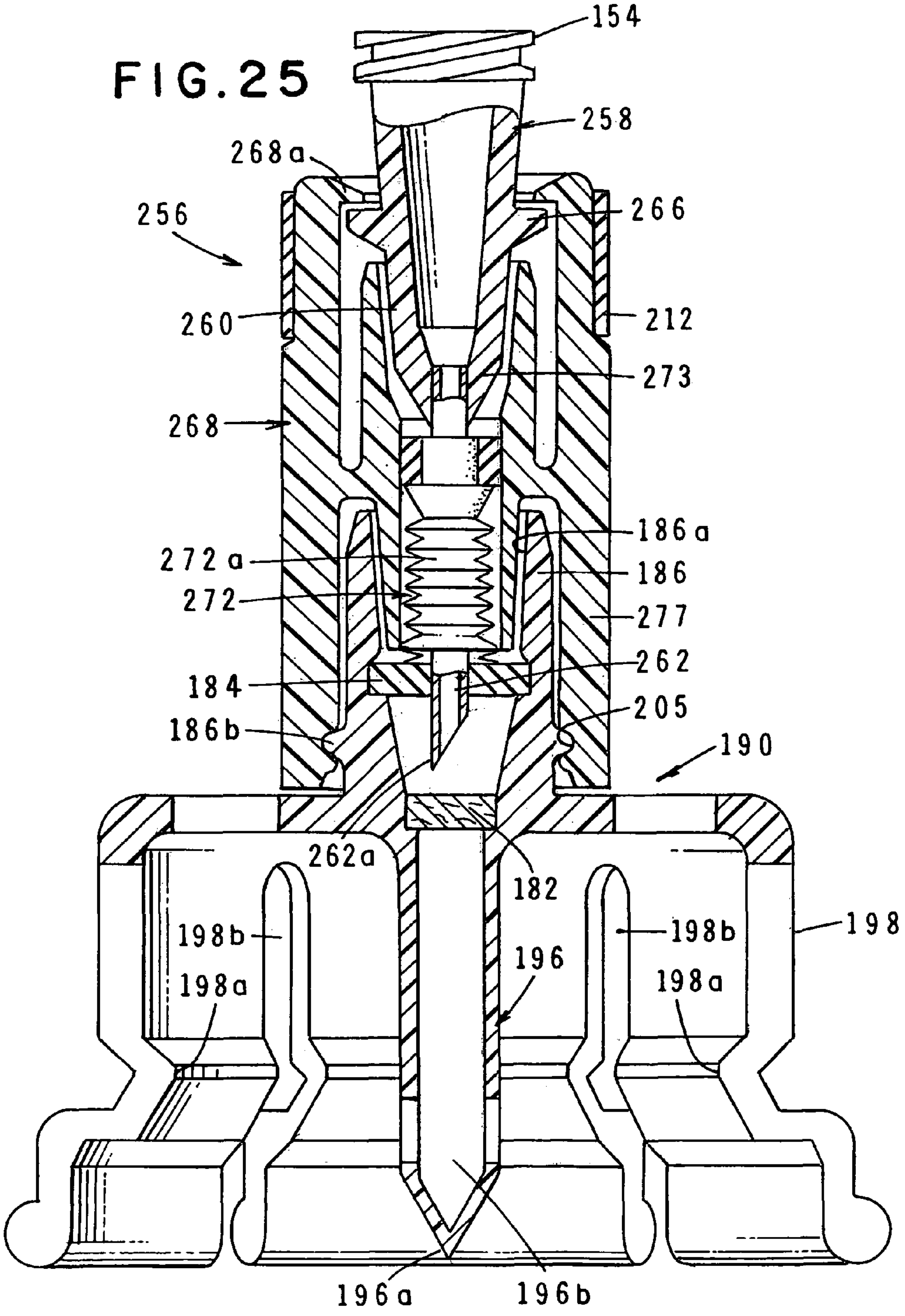
FIG. 25 is a side elevational view, partly in cross-section showing the form of vial accessing adapter subassembly of the invention that embodies the needle sheath component shown in FIG. 24.

Turning now to FIGS. 24 and 25 of the drawings, still another form of the vial accessing adapter means of the apparatus of the invention for the aseptic administration of medicaments contained within a medicament container. This alternate form of the invention, which is generally designated by the numeral 256, is somewhat similar to the embodiment shown in FIGS. 16 and 17 and like numerals are used in FIGS. 24 and 25 to identify like components. This latest form of the vial accessing adapter here comprises an aspirator or syringe connector assembly 258, that includes an outer wall 260 to which a downwardly extending hypodermic needle 262 having a piercing point 262*a* is connected. Provided proximate the upper end of outer wall 260 is a conventional luer connector 154 that permits the syringe connector assembly 258 to be interconnected with an appropriate aspirator such as the earlier described syringe 28 (FIG. 3). As previously mentioned, a unique feature of the syringe connector assembly, or aspirator connector 258, is the provision of a circumferentially extending, tapered locking rim 266 that functions to lockably engage the tapered flange 268*a* of the needle sheath 268 of this latest form of the invention when the aspirator connector is in position within the sheath.

The vial accessing adapter means of this latest form of the invention also includes filter means, shown here as a particulate filter 182, for filtering particulate matter from medicament aspirated from the medicament container. Additionally, although not necessary in this latest form of the invention, the vial accessing adapter means further includes a needle wiping member 184 that is connected to the neck portion 186 of the vial accessing adapter 190 of this latest form of the invention. Vial accessing adapter 190 is substantially identical in construction and operation to that described in connection with the embodiment of FIGS. 16 and 17.

As before, when the adapter component is mated with the medicament container, skirt 198 telescopically receives and securely grips the upper portion of the medicament container in a manner such that adapter cannula 196 will completely pierce the rubber stopper RS of the container (FIG. 2A) so as to open communication between the lumen of the cannula and the interior of the medicament container.

The primary difference between the aspirator connector 258 of this latest form of the invention and the aspirator connector of the embodiment of the invention shown in FIG. 17 of the drawings, resides in the provision of a collapsible needle protector 272 that is connected to the outer wall 260 of the aspirator connector. Collapsible needle protector 272 is movable from the first expanded position shown in FIG. 24 to the second collapsed position shown in FIG. 25. As indicated in FIG. 24 of the drawings, when the needle protector is in the first expanded position it encapsulates the downwardly extending needle 262 of the aspirator connector, including the piercing point 262*a*.

Needle protector 272, which includes a compressible, accordion like side wall 272*a*, is preferably constructed from a yieldable material and is constructed and arranged to fit snugly around the needle proximate the hub area 273 of the outer wall 260. With the unique construction thus described, when the aspirator connector 258 is mated with the needle sheath 268 in the manner illustrated in FIG. 25 of the drawings, the sidewall 272*a* of the needle protector is collapsed so as to expose the lower extremity of the needle 262. However, when the aspirator connector 258 is removed from the needle sheath, the snug fit collapsible needle protector will wipe the needle clean and will move into the expanded, needle protection configuration shown in FIG. 24 of the drawings. With the needle protector in this expanded configuration, it not only protects the needle from damage, but also importantly protects the user from needle stick.

Once the vial accessing adapter 190 is mated with the medicament container, the needle sheath 268 is mated with the adapter 190 by inserting the neck portion 186 of the adapter into the opening 275 defined by the skirt portion 277 of the needle sheath. With the vial accessing adapter of the invention in the configuration shown in FIG. 25, medicament can be drawn from the medicament container MC in the manner previously described herein. As the medicament is drawn from the container, it will be suitably filtered by the particulate filter 182.

Referring now to FIGS. 26 and 27, still another form of the vial accessing adapter subassembly of the invention is there shown and generally identified by the numeral 278. This latest adapter subassembly is similar to that illustrated in FIG. 1 of the drawings and like numerals are used in FIGS. 26 and 27 to identify like components. More particularly, the vial-accessing adapter subassembly 278 here includes an adapter component 14 that is substantially identical in construction and operation to that illustrated and described in connection with the embodiment of FIG. 1. Adapter component 14 includes a body portion 15 having a tapered bore 15*a*, a top wall 16 connected to the body portion, and an adapter cannula 18 that is integrally formed with and extends from body portion 15.

A container connector assembly 282 of the character illustrated in FIG. 26 of the drawings is also connected to top wall 16 and functions to removably interconnect the adapter component with a conventional medicament container MC (FIG. 2). The primary difference between the container connector means of this latest form of the invention and the connector means of the embodiment of FIG. 1, resides in the provision of a connector assembly 282 of a novel construction. Connector assembly 282 which is connectable to adapter component 14, here comprises a housing 284 that includes a downwardly extending protector sleeve 286 that is constructed and arranged to extend into the lumen 18*a* of the cannula 18 of the adapter component. As shown in FIG. 26, housing 284 houses the barrel portion 41 of the connector assembly 26, which is substantially identical in construction and operation to that illustrated in FIG. 1 of the drawings and earlier described herein. As depicted in FIG. 27 of the drawings, when the connector assembly 282 is mated with the adapter component 14, protector sleeve 286 extends into the lumen 18*a* of the adapter cannula 18 and circumscribes and substantially encapsulates the syringe cannula 42 of the connector assembly 26. With this novel construction the user can remove the syringe cannula from the drug vial and still maintain a protective covering that protects the syringe cannula from contamination. Additionally the protective covering 286 advantageously maintains the sharpness of the cannula and also effectively protects the user against needle stick.

In the manner illustrated in FIG. 27 of the drawings, the container connector assembly 282 of this latest form of the invention can be sealably connected to body portion 15 of the vial accessing adapter means of the invention and the apparatus can then be used in the manner previously described.

Having now described the invention in detail in accordance with the requirements of the patent statutes, those skilled in this art will have no difficulty in making changes and modifications in the individual parts or their relative assembly in order to meet specific requirements or conditions. Such changes and modifications may be made without departing from the scope and spirit of the invention, as set forth in the following claims.

The invention claimed is:

1. A vial accessing means for interconnecting an aspirator with a medicament container containing a medicament, comprising:

(a) an adapter including:
  (i) a top wall;
  (ii) a resiliently deformable skirt connected to and extending from said top wall in a first direction for receiving a portion of the medicament container;
  (iii) a connector extension connected to and extending from said top wall in a second direction, said connector extension having an outer wall and an inner wall defining a bore;
  (iv) an adapter cannula connected to and extending from said top wall in a first direction, said adapter cannula having a lumen in communication with said bore of said connector extension; and
  (v) a plurality of circumferentially spaced, buttress members connected to said resiliently deformable skirt, said plurality of buttress members defining an opening and being movable between a first position and a second position;
(b) a needle sheath received within said opening defined by said buttress members, said needle sheath being in engagement with said inner wall of said connector extension and including a yieldably deformable outer wall terminating in a generally annular shaped tapered flange defining an opening, said yieldably deformable outer wall being movable between a first position and a second position; and
(c) a syringe connector assembly for interconnection with an aspirator, said syringe connector assembly being lockably interconnected with said needle sheath.

2. The vial accessing means as defined in claim 1 in which said syringe connector assembly is received within said opening defined by said tapered flange and includes a needle having a piercing point and an outer wall having a circumferentially extending locking rim for lockably engaging said tapered flange of said needle sheath.

3. The vial accessing means as defined in claim 1 in which said needle of said syringe connector assembly comprises a blunt end cannula.

4. The vial accessing means as defined in claim 1 in which said adapter further includes filter means for filtering particulate matter from medicament aspirated from the medicament container.

5. The vial accessing means as defined in claim 1 in which said syringe connector assembly includes a luer connector.

6. The vial accessing means as defined in claim 1 in which said adapter includes a needle wiping member connected to said connector extension.

7. The vial accessing means as defined in claim 1 in which said needle sheath further includes an elastomeric band circumscribing said outer wall thereof for yieldably resisting movement of said outer wall between said first and second positions.

8. The vial accessing means as defined in claim 1 in which said needle sheath further includes an inner wall connected to said outer wall, said inner wall having an upper portion having tapered opening and a lower portion having a tapered outer wall.

9. The vial accessing means as defined in claim 8 in which said syringe connector assembly is sealably receivable within said tapered portion of said inner wall of said needle sheath.

10. The vial accessing means as defined in claim 8 in which said tapered outer wall of said lower portion of said needle sheath is sealably receivable within said connector extension of said adapter.

11. A vial accessing assembly for interconnecting an aspirator with a medicament container containing a medicament, comprising:

(a) an adapter including:
  (i) a top wall;
  (ii) a resiliently deformable skirt connected to and extending from said top wall in a first direction for receiving a portion of the medicament container;
  (iii) a connector extension connected to and extending from said top wall in a second direction, said connector extension having an outer wall and a inner wall defining a tapered bore;
  (iv) an adapter cannula connected to and extending from said top wall in a first direction, said adapter cannula having a lumen in communication with said bore of said connector extension; and
  (v) a plurality of circumferentially spaced, buttress members connected to said resiliently deformable skirt, said plurality of buttress members defining an opening and being movable between a first position and a second position;
(b) a needle sheath received within said opening defined by said buttress members, said needle sheath being in engagement with said inner and outer walls of said connector extension and including:
  (i) a yieldably deformable outer wall terminating in a generally annular shaped tapered flange defining an opening, said yieldably deformable outer wall being movable between a first position and a second position;
  (ii) an elastomeric band circumscribing said outer wall for yieldably resisting movement of said outer wall between said first and second positions; and
  (iii) an inner wall connected to said outer wall, said inner wall having an upper portion having tapered opening and a lower portion having a tapered outer wall; and
(c) an aspirator connector for interconnection with an aspirator, said aspirator connector being received within said opening defined by said tapered flange of said needle sheath and including:

(i) an outer wall having a circumferentially extending locking rim for lockably engaging said tapered flange of said needle sheath;

(ii) a luer connector connected to said outer wall; and (iii) a needle connected to and extending from said outer wall.

12. The vial accessing assembly as defined in claim 11 which said adapter further includes filter means for filtering particulate matter from medicament aspirated from the medicament container.

13. The vial accessing means as defined in claim 11 in which said needle of said aspirator connector comprises a blunt end cannula.

14. The vial accessing assembly as defined in claim 11 in which said adapter further includes a needle wiping member connected to said connector extension.

15. The vial accessing assembly as defined in claim 11 in which said tapered outer wall of said lower portion of said needle sheath is sealably receivable within said connector extension of said adapter.

16. A vial accessing assembly for interconnecting an aspirator with a medicament container containing a medicament, comprising:

(a) an adapter including:

(i) a top wall;

(ii) a resiliently deformable skirt connected to and extending from said top wall in a first direction for receiving a portion of the medicament container;

(iii) a connector extension connected to and extending from said top wall in a second direction, said connector extension having an outer wall and a inner wall defining a tapered bore;

(iv) an adapter cannula connected to and extending from said top wall in a first direction, said adapter cannula having a lumen in communication with said bore of said connector extension;

(v) a plurality of circumferentially spaced, buttress members connected to said resiliently deformable skirt, said plurality of buttress members defining an opening and being movable between a first position and a second position;

(vi) filter means for filtering particulate matter from medicament aspirated from the medicament container; and (vii) a needle wiping member connected to said connector extension;

(b) a needle sheath received within said opening defined by said buttress members, said needle sheath being in engagement with said outer wall of said connector extension and including:

(i) a yieldably deformable outer wall terminating in a generally annular shaped tapered flange defining an opening, said yieldably deformable outer wall being movable between a first position and a second position;

(ii) an elastomeric band circumscribing said outer wall for yieldably resisting movement of said outer wall between said first and second positions; and (iii) an inner wall connected to said outer wall, said inner wall having an upper portion having a tapered opening and a lower portion having a tapered outer wall; and (c) an aspirator connector for interconnection with an aspirator, said aspirator connector being received within said opening defined by said tapered flange of said needle sheath and including:

(i) an outer wall having a circumferentially extending locking rim for lockably engaging said tapered flange of said needle sheath;

(ii) a luer connector connected to said outer wall; and (iii) a needle connected to and extending from said outer wall.

17. The vial accessing means as defined in claim 16 in which said needle of said aspirator connector comprises a blunt end cannula.

18. The vial accessing assembly as defined in claim 16 in which said tapered outer wall of said lower portion of said needle sheath is sealably receivable within said connector extension of said adapter.

19. The vial accessing assembly as defined in claim 16 in which said yieldably deformable outer wall of said needle sheath is provided with diametrically opposed, longitudinally extending slits.

20. The vial accessing assembly as defined in claim 16 in which said needle sheath is constructed from a moldable plastic.

21. The vial accessing assembly as defined in claim 16 in which said yieldably deformable outer wall of said needle sheath includes a lower portion, said lower portion being movable between a first position wherein said aspirator connector is locked within said needle sheath and a second position wherein said aspirator connector can be removed from said needle sheath.

22. The vial accessing assembly as defined in claim 16 in which said yieldably deformable outer wall of said needle sheath includes a circumferentially extending bead, said bead being engagable with said yieldably deformable outer wall of said needle sheath upon said needle sheath being received within said opening defined by said buttress members to impart a tactile sensation.

23. A method for injecting medicaments into the patient using an apparatus comprising a vial accessing means for interconnecting an aspirator with a medicament container having an interior containing a medicament, the vial accessing means including an adapter having a top wall, a resiliently deformable skirt connected to and extending from the top wall for receiving a portion of the medicament container and an adapter cannula connected to and extending from the top wall and a plurality of circumferentially spaced, buttress members defining an opening; and an assembly made up of a needle sheath having a yieldably deformable wall and a syringe connector assembly for interconnection with an aspirator, the assembly being received within the opening defined by the buttress members; said method comprising the steps of:

(a) mating the adapter with the medicament container in a manner to place the adapter cannula in communication with the interior of medicament container;

(b) attaching the aspirator to the assembly made up of the needle sheath and the syringe connector assembly to form an aspiration assembly;

(c) inserting the assembly made up of the needle sheath and the syringe connector assembly into the opening defined by the buttress members;

(d) using the aspirator, withdrawing the medicament from the container;

(e) removing the aspiration assembly from the adapter;

(f) yieldably deforming the wall of the needle sheath and removing the syringe connector assembly from the needle sheath to form a combination aspirator and syringe connector assembly; and (g) using the combination aspirator and syringe connector assembly, injecting the medicament into the patient.

* * * * *